(12) United States Patent
Chaudhuri

(10) Patent No.: US 8,003,082 B2
(45) Date of Patent: *Aug. 23, 2011

(54) PHOTOSTABLE ORGANIC SUNSCREEN COMPOSITION

(75) Inventor: Ratan Chaudhuri, Lincoln Park, NJ (US)

(73) Assignee: Merck Patent GmbH, Darmstadt (DE)

( * ) Notice: Subject to any disclaimer, the term of this patent is extended or adjusted under 35 U.S.C. 154(b) by 1080 days.

This patent is subject to a terminal disclaimer.

(21) Appl. No.: 10/559,291

(22) PCT Filed: May 27, 2004

(86) PCT No.: PCT/EP2004/005716
§ 371 (c)(1),
(2), (4) Date: Mar. 31, 2006

(87) PCT Pub. No.: WO2004/105712
PCT Pub. Date: Dec. 9, 2004

(65) Prior Publication Data
US 2007/0059258 A1    Mar. 15, 2007

Related U.S. Application Data

(63) Continuation-in-part of application No. 10/452,199, filed on Jun. 3, 2003, now Pat. No. 7,166,273.

(51) Int. Cl.
*A61Q 17/00* (2006.01)
*A61Q 17/04* (2006.01)
*A61Q 19/00* (2006.01)
*A61K 8/00* (2006.01)

(52) U.S. Cl. ............. 424/59; 424/60; 424/400; 424/401
(58) Field of Classification Search .................. 424/59, 424/60, 400, 401
See application file for complete search history.

(56) References Cited

U.S. PATENT DOCUMENTS

| | | | | |
|---|---|---|---|---|
| 4,444,755 | A * | 4/1984 | Horrobin | 424/642 |
| 5,672,337 | A * | 9/1997 | Ascione et al. | 424/59 |
| 5,830,441 | A * | 11/1998 | Wang et al. | 424/59 |
| 6,238,650 | B1 * | 5/2001 | Lapidot et al. | 424/59 |
| 6,242,099 | B1 * | 6/2001 | Grandmontagne et al. | 428/402.2 |
| 6,303,149 | B1 * | 10/2001 | Magdassi et al. | 424/489 |
| 6,436,375 | B1 | 8/2002 | Lapidot et al. | |
| 7,166,273 | B2 * | 1/2007 | Chaudhuri | 424/59 |
| 2002/0104122 | A1 | 8/2002 | Kakitani et al. | |
| 2003/0108492 | A1 | 6/2003 | Chaudhuri | |

FOREIGN PATENT DOCUMENTS

| | | |
|---|---|---|
| WO | WO 0071084 | 11/2000 |
| WO | WO 0072806 | 12/2000 |
| WO | WO 0124762 | 4/2001 |
| WO | WO 03007906 | 1/2003 |

* cited by examiner

*Primary Examiner* — Johann Richter
*Assistant Examiner* — Luke Karpinski
(74) *Attorney, Agent, or Firm* — Millen, White, Zelano & Branigan, P.C.

(57) ABSTRACT

The present invention relates to a sunscreen capsule comprising i) at least one UV-A organic sunscreen and ii) at least one photostabilizer, furthermore it relates to a composition for topical application comprising these capsule and methods of production and use of these capsules and compositions.

37 Claims, No Drawings

PHOTOSTABLE ORGANIC SUNSCREEN COMPOSITION

This application is a National Phase of PCT No. PCT/EP2004/005716 filed on May 27, 2004, which is a continuation-in-part of Ser. No. 10/452,199 filed on Jun. 3, 2003 now U.S. Pat. No. 7,166,273.

This application is related to U.S. patent application Ser. Nos. 09/904,904 (filed Jul. 16, 2001; published under No. US20030108492A1) and 10/022,343 (filed Dec. 20, 2001; published under No. US20030157035A1). For purpose of the United States national phase: This application is a continuation-in-part of application Ser. No. 10/452,199, filed Jun. 3, 2003, by Chaudhuri, Ratan K., entitled Photostable Organic Sunscreen Composition.

The present invention relates to a sunscreen capsule comprising i) at least one UV-A organic sunscreen and ii) at least one photostabilizer; furthermore it relates to a composition for topical application comprising the capsule and methods of production and use of these capsules and compositions.

BACKGROUND OF THE INVENTION

Topical sunscreen compositions are commonly used during outdoor work or leisure as a means for providing protection of exposed skin against acute and chronic adverse effects of solar radiation such as, for example, sunburn, cancer and photo-aging. Many effective sunscreen preparations are sold commercially or are described in cosmetic or pharmaceutical literature. In general, sunscreen preparations are formulated as creams, lotions or oils containing as the active agent an ultra violet radiation absorbing chemical compound. The sunscreen functions by blocking passage of ultra violet radiation thereby preventing its penetration into the skin.

According to Zecchino et al. (U.S. Pat. No. 5,008,100), sunscreen agents may be characterized in the order of decreasing effectiveness as either highly chromophoric (monomeric organic compounds and inorganic compounds such as titanium dioxide) and minimally chromophoric (polymeric organic solids).

Organic sunscreens are classified into UV-A filters, UV-B filters or broad spectrum filters (UV-A and UV-B functionality in a single molecule) depending on the type of radiation they absorb. UV-A sunscreens absorb radiation in the 320 to 400 nm regions of the ultra violet spectrum and UV-B sunscreens absorb radiation in the 290 to 320 nm regions of the ultra violet spectrum.

Broad band sunscreens (UV-A and UV-B functionality) absorb radiation in the 290 to 400 nm region of the ultra violet spectrum and have two maximums, one in the UV-B region and the other in the UV-A region.

Representative references related to UV sunscreens are:

U.S. Pat. No. 3,278,448, which discloses cinnamic acid derivatives such as 4-hydroxy, 3-5-ditertbutyl-alphacarbethoxy-cinnamic acid ether ester in column 2, line 20;

U.S. Pat. No. 3,538,226, which describes cinnamic acid alkyl ester derivatives at column 1, lines 15-31 and column 2, lines 1-12 and column 3, lines 30-55 and 60;

U.S. Pat. No. 5,175,340, which describes cinnamic acid alkyl esters having hydroxy radicals and alkoxy radicals on the phenyl ring, and U.S. Pat. No. 5,830,441, which describes UV absorbents containing a cyano or cinnamyl moiety by the generic formula at col. 2, lines 1-21.

Other references which disclose cinnamide compounds include U.S. Pat. Nos. 5,601,811, 4,335,054, 5,124,354, 5,294,643 and 5,514,711.

Unfortunately, some of the highly chromophoric monomeric organic compounds employed in sunscreen compositions or capsules are not photostable and the protection from sun damage is lost. For example dibenzoylmethane derivatives, such as Avobenzone, a UV-A sunscreen, are generally photo-unstable. Furthermore, photo-instability of Avobenzone increases significantly when combined with Octyl methoxycinnamate (UV-B organic sunscreen). In most studies, Octyl methoxycinnamte (OMC) has been regarded as relatively photostable. The absorption maxima of Avobenzone (~360 nm) and OMC (~310 nm) do not overlap sufficiently to allow directly excited singlet-singlet energy transfer to occur. However, transfer from one excited triplet-state to another is possible provided the energy levels are suitable.

The triplet-state of OMC has been shown to quench the triplet-states of 8-methoxy psoralen and 5-methoxy psoralen, subsequently undergoing E/Z isomerization (Morliere P., O. Avice, T. S. Melo, L. Dubertret, M. Giraud and R. Santus, A study of the photochemical properties of some cinnamte sunscreens by steady state and flash photolysis. Photochem. Photobiol, 36, 395-399 (1982); Morliere P., G. Huppe, D. Averbeck, A. R. Young, R. Santus, and L. Dubertret, In-vitro photostability and photosensitizing properties of bergamot oil. Effects of a cinnamte sunscreen. J. Photochem. Photobiol. B, Biol, 7, 199-208 (1990)). This is clearly evident that the triplet state of OMC is accessible to triplet energy transfer and that subsequent chemistry occurs.

The triplet-state of Avobenzone is surprisingly accessible and allowing energy transfer to other nearby molecules having triplet states with suitable overlap; the presence of OMC provides a suitable target acceptor. OMC undergoes E/Z photoisomerization upon accepting triplet state energy transfer and subsequent photolysis of OMC. It would appear that photo-instability of Avobenzone may cause the photolysis of OMC when they are combined together. This limits obtaining a broad-spectrum (ITV-A and UV-B) sunscreen composition or capsule combining dibenzoylmethane derivatives, such as Avobenzone with Octyl methoxycinnamte.

In addition to lack of photostability of many organic sunscreens, they do not possess an antioxidant property, which protects skin or hair.

The ideal sunscreen formulation/composition should be nontoxic and non-irritating to the skin tissue and be capable of convenient application in a uniform continuous film. The product should be chemically and physically stable so as to provide an acceptable shelf life upon storage. It is particularly desirable that the preparation should retain its protective effect over a prolonged period after application. Thus, the active agent when present on the skin must be resistant to chemical and/or photo degradation.

Techniques for stabilizing UV absorbent compositions are known. Representative disclosures in this area include U.S. Pat. Nos. 5,567,418; 5,538,716; 5,951,968 and 5,670,140.

Antioxidants are believed to function by providing protection from free-radical damage. To be an effective quencher, it is believed the antioxidant must be present in an adequate concentration at the site of free radical generation. Since antioxidants are used in low concentrations and are a separate ingredient, they may not be available at the site of generation, thereby reducing the desired level of skin protection. Based on these drawbacks, it is desirable to provide a photostable sunscreen composition or capsule wherein a photostablizer having an antioxidant and sunscreen functionality in a single molecule is present to enhance the effectiveness of the protection of skin, hair, paints, fibers, wood, plastics, polymers, color, colored wax-based articles, etc. against sun damage.

A new class of photostabilizers suitable to stabilize dibenzoylmethane derivatives is known from the international patent application WO2003/007906A. The most preferred photostabilizers disclosed there are dialkylbenzalmalonates or derivatives thereof.

SUMMARY OF THE INVENTION

Thus, the present invention relates to a capsule comprising (a1) at least one UV-A organic sunscreen and (b) at least one photostabilizer.

The capsule optionally contains (a2) at least one UV-B liquid organic sunscreen and/or (c) at least one solubilizer, and/or (d) at least one cosmetically or pharmaceutically acceptable carrier. An especially preferred composition comprises (a1), (a2), (b) and/or (c) and optionally (d).

Furthermore, the present invention relates to a composition suitable for topical application comprising the sunscreen capsule described above and at least a carrier suitable for topical application.

The sunscreen capsules described above are usually present in an amount necessary to provide 0.5 to 10% by weight of the whole composition preferably 1-8% by weight of the UV-A organic sunscreen.

In the capsule said at least one UV-A organic sunscreen and said at least one photostabilizer are usually present in a weight-ratio from about 3:1 to about 1:3, preferably from about 1:0.8 to 1:2.

In a particular embodiment, the present invention relates to a photostable sunscreen composition or capsule comprising at least one UV-A organic sunscreen which belongs to the class of dibenzoylmethane or a derivative thereof; at least one photostabilizer belonging to the class of dialkylbenzalmalonate or a derivative thereof; at least one UV-B liquid organic sunscreen preferably belonging to the class of salicylates or cinnamates or a combination thereof and/or at least one solubilizer which preferably is an ester, a long chain fatty acid or an alcohol; and optionally at least one cosmetically or pharmaceutically acceptable carrier.

The sunscreen capsules may optionally contain one or more long chain fatty alcohols or esters or amides or combination thereof, preferably liquid in nature and able to solubilize the UV A organic sunscreen preferably to at least 15%. These alcohols or esters can be used alone or in combination as a co-solubilizer with organic UV-B sunscreens. Exemplary long chain alcohols or esters according to the present invention include: cocoglycerides, decyloleate, C-12-15 alkyl benzoate, caprylic/capric triglycerides, cetaryl ethylhexylhexanoate, dioctyl adipate, glyceryl dilaurate, stearamide, dimethylbehanamide, b-alanin derivatives, such as, ethyl butylacetylamino propoane (IR 3535) etc. A long chain fatty alcohol or ester is typically present in the capsule in an amount ranging from 0 to 80%.

It is advantageous to use organic UV filters in encapsulated form. Specifically, the following advantages can arise by encapsulation:

The hydrophilicity of the capsule wall can be set independently of the solubility of the UV filter. First, for example, it is possible to incorporate even hydrophobic UV filters into purely aqueous formulations. In addition, the oily impression which is often perceived as unpleasant upon application of the preparation comprising hydrophobic UV filters is prevented.

Certain UV A filters, in particular dibenzoylmethane derivatives, exhibit only reduced photostability in cosmetic formulations. By encapsulating these filters or compounds which impair the photostability of these filters, such as, for example, the above-mentioned cinnamic acid derivatives, it is possible to increase the photostability of the overall formulation. By encapsulation the dibenzoylmethane derivatives together with an additional photostabilizer the photostability of the overall formulation can further be improved.

The literature discusses again and again the penetration of the skin by organic UV filters and the irritancy potential associated therewith upon direct application to the human skin. The encapsulation of the corresponding substances proposed here overcomes the problem of skin penetration.

Sunscreen products are widely used all over the world by all ages and gender, however, not only that some of the active ingredients in these products are said to possibly cause contact dermatitis, but also the light-excited species of some of these reagents might cause photocontact dermatitis. In addition, some sunscreen compounds also enhance generation of singlet oxygen under sun light. Thus, encapsulating sunscreen active ingredients in a transparent matrix like silica offers a sophisticated way to benefit from the light-absorbing capability of sunscreens, while substantially isolating them and/or their possible photodecomposition products from the live tissues.

Generally, by encapsulating individual UV filters or other ingredients, it is possible to avoid formulation problems, which arise as a result of interaction of individual formulation constituents with one another, such as crystallization processes, precipitations and agglomeration, since the interaction is prevented. In one preferred embodiment of the invention the UV A sunscreen and the photostabilizer are encapsulated together with a solubilizing agent to further optimize sunscreen performance of these ingredients.

According to the invention therefore a UVA filter, the photostabilizer and optionally one or more of the additional above-mentioned UV filters are present in encapsulated form. It is furthermore advantageous if the capsules are so small that they cannot be observed with the naked eye. To achieve the above-mentioned effects, it is also necessary for the capsules to be sufficiently stable and not to release the encapsulated active ingredient (UV filter) into the surroundings, or to release it only to a minor extent.

Suitable capsules can have walls made of inorganic or organic polymers. For example, U.S. Pat. No. 6,242,099 B1 describes the preparation of suitable capsules with balls made of chitin, chitin derivatives or polyhydroxylated polyamines.

Capsules which are to be used particularly preferably according to the invention have walls which can be obtained by a sol-gel process, as is described in the applications WO 00/09652, WO 00/72806 and WO 00/71084. Preference is given here in turn to capsules whose walls are made of silica gel (silica; undefined silicon oxide hydroxide). The preparation of corresponding capsules is known to the person skilled in the art, for example, from the cited patent applications, the contents of which also expressly belonging to the subject-matter of the present application.

In another preferred embodiment the capsules have a capsule wall that is mainly composed of organopolysiloxane. Methods to produce capsules with organopolysiloxane walls are for example described in U.S. Pat. No. 6,337,089 and U.S. Pat. No. 6,252,313 and included herein by reference. Preferably the organopolysiloxane is synthesized by polycondensing one or more compounds represented by the general formula:

$$R_n Si(OH)_m Y_{(4-m-n)}$$

wherein, m represents an integer from 1 to 4 and n represents an integer from 0 to 3 with the condition that $m+n \leq 4$; R represents an organic group in which a carbon atom is directly connected to a silicone atom, and when n is greater than 1, each of the R groups may be the same or different; and Y represents at least one group selected from the group consisting of an alkoxy group, hydrogen and siloxy group, and when (4-m-n) is greater than 1, each of the groups Y may be the same or different.

For increasing the photostability, the sunscreen capsules of the invention are preferably prepared via a sol-gel encapsulation process as described in U.S. Pat. Nos. 6,468,509; 6,436,375; and 6,238,650.

Accordingly, a method of producing a sunscreen capsule by mixing at least one UV-A organic sunscreen and at least one photostabilizer with a precursor material for the capsule wall and forming the wall by condensing the precursor is a further embodiment of the invention.

In one preferred embodiment, the method implies the polycondensation of the precursor occurs during a sol gel process.

In another preferred embodiment of the method the precursor is a polysiloxane prepolymer.

Exemplary dibenzoylmethane derivatives according to the present invention include but are not limited to 2-Methyldibenzoylmethane, 4-Methyldibenzoylmethane, 4-Isopropyldibenzoylmethane, 4-Tert-butyldibenzoylmethane, 2,4-Dimethyldibenzoylmethane, 2,5-Dimethyldibenzoylmethane, 4,4'-Diisopropyldibenzoylmethane, 4,4'-Dimethyldibenzoylmethane, 4-Tert-butyl-4'-methoxydibenzoylmethane, 2-Methyl-5-isopropyl-4'-methoxydibenzoylmethane, 2-Methyl-5-tert-butyl-4'-methoxydibenzoylmethane, 2,4-Dimethyl-4'-methoxydibenzoylmethane, 2,6-Dimethyl-4-tert-butyl-4'-methoxydibenzoylmethane.

Particularly preferred is 4-(tert-butyl)-4'-methoxydibenzoylmethane also identified as 1(p-tert butylphenyl)-3-(p-methoxyphenyl)-1,3-propanedione CAS 70356-09-1 (the generic name being Avobenzone), commercially available under the trademark "Parsol 1789" by Roche or "Eusolex 9020" by Merck KGaAIEMD Chemicals. This sunscreen has the following structural formula.

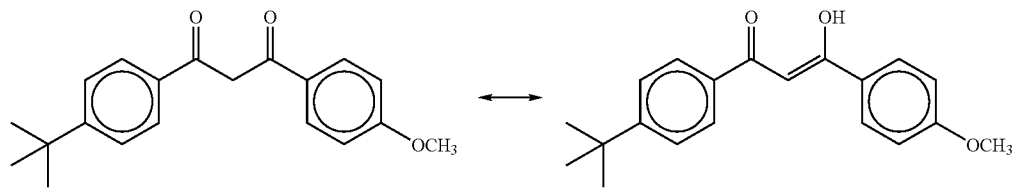

The enol-form of Avobenzone is the preferred sunscreen.

The dibenzoylmethane derivative or derivatives can be present in the preferred composition in a concentration ranging from 0.5% to 35% by weight and preferably ranging from 10% to 25% by weight with respect to the total weight of the composition.

The photostabilizer compounds of the composition are usually compounds with sunscreen activity, i.e. they are chromophoric within the ultra violet radiation range of from 290-400 nm and also exhibit antioxidant properties.

Preferably the photostabilizers are selected among those disclosed in WO2003/007906A, the contents of which expressly belongs to the subject-matter of the present application.

Furthermore, the photostabilizer is preferably a compound of formula I or

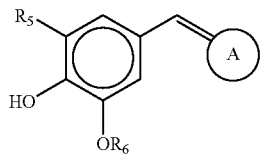

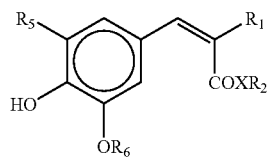

wherein
A is a moiety which provides chromophoric properties;
$R_1$ is selected from the group consisting of —C(O)CH$_3$, —CO$_2$R$_3$, —C(O)NH$_2$, —C(O)N(R$_4$)$_2$ and —CN;
X is O or NH or N—C$_{1-8}$-Alkyl;
$R_2$ is linear or branched C$_1$ to C$_{20}$ alkyl;
$R_3$ is linear or branched C$_1$ to C$_{20}$ alkyl; and
each $R_4$ is independently hydrogen or linear or branched C$_1$ to C$_8$ alkyl.
$R_5$ is hydrogen or linear or branched C$_1$-C$_8$ alkyl or linear or branched C$_1$-C$_8$ alkoxy,
$R_6$ is independently linear or branched C$_1$-C$_8$ alkyl.

A in formula I is preferably a moiety which is chromophoric within the UV radiation range of wavelengths to provide UV absorbing activity to the compound of formula I, wherein moiety A comprises one divalent group or two monovalent groups, with at least one group having carbonyl (C=O) functionality.

In a preferred embodiment —R$_5$ and —O—R$_6$ are independently of each other selected from linear or branched C$_1$-C$_8$ alkoxy radicals, and wherein preferably the at least one compound of formula I or II is at least one compound selected from the compounds of formula III or IV

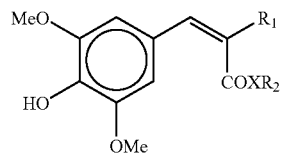

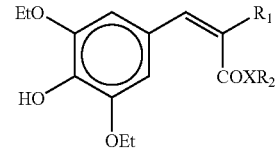

wherein
R₁ is selected from the group consisting —C(O)CH₃, —CO₂ (C₁-C₈ alkyl), —C(O)NH₂, —C(O)NH(C₁-C₄ alkyl), —C(O)N(C₁-C₄ alkyl)₂ and —CN;
X is O or NH or N—C₁₋₈-Alkyl; and
R₂ is C₁-C₁₂ alkyl.

A preferred capsule according to the invention comprises at least one compound of formula I or II is at least one compound selected from the compounds of formula V or VI

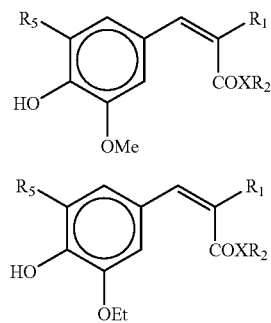

wherein
R₁ is selected from the group consisting —C(O)CH₃, —CO₂ (C₁-C₈ alkyl), —C(O)NH₂, —C(O)N(C₁-C₄ alkyl)₂, and —CN;
X is O or NH or N—C1-8-Alkyl; and
R₂ is C₁-C₁₂ alkyl, and
R₅ is C₁-C₈ linear or branched alkyl.

Another preferred capsule comprises at least one compound of formula I or II, wherein —R₅ and —O—R₆ are independently of each other linear or branched C₁-C₄ alkoxy, and wherein preferably —R₅ and —O—R₆ are identical and are either methoxy or ethoxy.

Another preferred capsule comprises at least one compound of formula I or II, wherein X is oxygen and R₂ is preferably linear or branched C₁-C₄ alkyl.

Another preferred capsule comprises at least one compound of formula I or II, wherein R₁ is CO₂R₃, preferably C(O)CH₃, and, R₃ is linear or branched C₁ to C₄ alkyl.

Another preferred capsule comprises at least one compound of formula I or II, wherein R₁ is —C(O)N(R₄)₂, and at least one R₄ is hydrogen and the other is hydrogen or linear or branched C₁ to C₄ alkyl.

Another preferred capsule comprises at least one compound of formula I or II, wherein R₁ is —C(O)N(R₄)₂, and each R₄ is independently linear or branched C₁ to C₄ alkyl.

Another preferred capsule comprises at least one compound of formula I or II, wherein X is N-Methyl or N-Ethyl.

Another preferred capsule comprises at least one compound of formula I or II, wherein at least one of R₂ and R₃ is linear or branched C₈ to C₂₀ alkyl, and wherein preferably R₂ and R₃ are each linear or branched C₈ alkyl or at least one of R₂ and R₃ is linear or branched C₁₂ to C₂₀ alkyl.

Another preferred capsule comprises at least one compound of formula I or II, wherein said compound of formula I or II is selected from the group consisting of
ethyl-alpha-acetyl-3,5-dimethoxy-4-hydroxy cinnamate,
iso-propyl-alpha-acetyl-3,5-dimethoxy-4-hydroxy cinnamate,
iso-amyl-alpha-acetyl-3,5-dimethoxy-4-hydroxy cinnamate,
2-ethylhexyl-alpha-acetyl-3,5-dimethoxy-4-hydroxy cinnamate,
diethyl-3,5-dimethoxy-4-hydroxy benzylidene malonate,
di-(2-ethylhexyl)-3,5-dimethoxy-4-hydroxy benzylidene malonate,
diisoamyl-3,5-dimethoxy-4-hydroxy benzylidene malonate,
dipalmitoyl-3,5-dimethoxy-4-hydroxy benzylidene malonate,
di-dodecyl-3,5-dimethoxy-4-hydroxy benzylidene malonate,
di-isopropyl-3,5-dimethoxy-4-hydroxy benzylidene malonate,
ethyl-alpha-cyano-3-methoxy-4-hydroxy cinnamate,
ethyl-alpha-acetyl-3-methoxy-4-hydroxy cinnamate,
iso-propyl-alpha-acetyl-3-methoxy-4-hydroxy cinnamate,
iso-amyl-alpha-acetyl-3-methoxy-4-hydroxy cinnamate,
2-ethylhexyl-alpha-acetyl-3-methoxy-4-hydroxy cinnamate,
diethyl-3-methoxy-4-hydroxy benzylidene malonate,
di-(2-ethylhexyl)-3-methoxy-4-hydroxy benzylidene malonate,
diisoamyl-3-methoxy-4-hydroxy benzylidene malonate,
dipalmitoyl-3-methoxy-4-hydroxy benzylidene malonate,
di-dodecyl-3-methoxy-4-hydroxy benzylidene malonate,
di-isopropyl-3-methoxy-4-hydroxy benzylidene malonate,
di-(2-ethyhexyl)-3-methoxy-4-hydroxy-5-isopropyl-benzylidene malonate,
di-isoamyl-3-methoxy-4-hydroxy-5-tert.butyl-benzylidene malonate,
iso-amyl-alpha-acetyl-3-methoxy-4-hydroxy-5-isopropyl cinnamate, and
iso-amyl-alpha-acetyl-3-methoxy-4-hydroxy-5-tert.butyl cinnamate.

The one or more compounds of formula I or II can preferably stabilize an additional sunscreening agent against photodegradation from exposure to sunlight.

Preferred compounds are of formula IIa below.

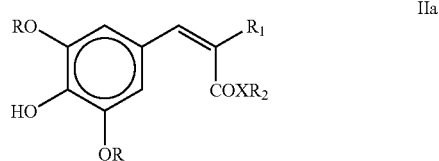

wherein,
each R is independently linear or branched C₁ to C₈ alkyl;
R₁ is selected from the group consisting of —C(O)CH₃, —CO₂R₃, —C(O)NH₂, and
C(O)N(R₄)₂. and —CN;
X is O or NH or N—C₁₋₈-Alkyl;
R₂ is linear or branched C₁ to C₂₀ alkyl;
R₃ is linear or branched C₁ to C₂₀ alkyl; and
each R₄ is independently hydrogen or linear or branched C₁ to C₈ alkyl.

Included within the preferred compounds are those of formula IIa wherein R is linear or branched C₁-C₄ alkyl, X is oxygen and R₂ is linear or branched C₁-C₁₂ alkyl. Of these compounds, those more preferred have R₁ as C(O)CH₃ or CO₂R₃ wherein R₃ is a linear or branched C₁ to C₄ alkyl. For compounds wherein R₁ is C(O)N(R₄)₂, R₄ is preferably hydrogen or a linear or branched C₁-C₄ alkyl.

While compounds having from C₁-C₄ alkyl groups for R₂ and R₃ are preferred, significant utility can be obtained from compounds wherein R₂ and R₃ are linear or branched C₈ to C₂₀ alkyl or C₁₂ to C₂₀ alkyl groups.

A preferred class of compounds is that of formulae III or IV wherein R₁ and R₂ are as defined for formula I with R₃ is C₁-C₈ alkyl and R₄ is C₁-C₄ alkyl.

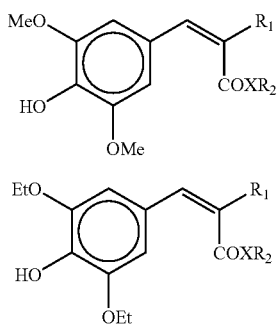

The one or more compounds of formula I or II can preferably stabilize a sunscreen agent against photodegradation from sun exposure to sunlight.

Included within the preferred compounds are those of formula II wherein $R_1$ is linear or branched $C_1$-$C_4$ alkyl, X is oxygen and $R_2$ is linear or branched $C_1$-$C_{12}$ alkyl. Of these compounds, those more preferred have $R_1$ as $C(O)CH_3$ or $CO_2R_3$ wherein $R_3$ is a linear or branched $C_1$ to $C_4$ alkyl. For compounds wherein $R_1$ is $C(O)N(R_4)_2$, $R_4$ is preferably hydrogen or a linear or branched $C_1$-$C_4$ alkyl.

While compounds having from $C_1$-$C_4$ alkyl groups for $R_2$ and $R_3$ are preferred, significant utility can be obtained from compounds wherein $R_2$ and $R_3$ are linear or branched $C_8$ to $C_{20}$ alkyl or $C_{12}$ to $C_{20}$ alkyl groups.

In the following passage it is sometimes referred to the compositions suitable for topical application as sunscreen formulations or sunscreen compositions. This is due to the fact that these compositions necessarily contain at least on encapsulated UV A sunscreen compound. Nevertheless compositions according to the present invention are not necessarily marketed as sunscreen formulations. The compositions can for example also be marketed as day care, skin care, hair care or personal care compositions.

The present invention also provides sunscreen formulations, which comprise at least one compound of formula I-VI. Amounts of the compounds of formula I-VI within such compositions typically range from 0.1 to 40 wt % based on the total weight of the sunscreen. These sunscreen formulations can contain one or more additional organic sunscreen agents for filtering UV-B and/or UV-A rays or they may additionally contain one or more metal oxide sunscreen agents such as titanium dioxide or zinc oxide.

These sunscreen formulations may additionally contain a carrier and at least one component selected from the group consisting of dispersing agents, preservatives, anti-foams, perfumes, oils, waxes, propellants, dyes, pigment emulsifiers, surfactants, thickeners, humectants, exfoliants and emollients. These sunscreen formulations may be in the form of a cosmetic composition with a cosmetically acceptable carrier and one or more cosmetic adjuvants. The sunscreen formulation can optionally have conventional antioxidants or other stabilizers, which do not have UV absorbing characteristics.

Methods of using these sunscreen compositions or capsules and methods for improving the photostability of sunscreen formulations are also provided. The methods of using the sunscreen formulations comprise applying a sunscreen formulation, which contains a compound of formula I-VI to a substrate. Preferred substrates are skin and hair. Other substrates include, but are not limited to paints, fibers, wood, plastics, polymers, color, colored wax-based articles, etc. whereby a composition of the invention is applied to such substrates or mixed in during the preparation of such substrates.

To improve the photostability of a sunscreen formulation, especially a sunscreen formulation within a capsule, a compound of formula I-VI is added to the sunscreen formulation in an amount sufficient to reduce the loss of UV absorbance of the sunscreen as it is irradiated. Typical amounts fall within the range of 0.1% to 40 wt %, based on the total weight of said sunscreen formulation. More typically, the amount falls within the range of 1 wt % to 25 wt %. The amount of organic sunscreen compound of formulae I-VI, preferably ranges from about 3 wt % to about 15 wt % of the sunscreen formulation. Other ingredients referred to above and discussed more particularly below are each generally used in an amount from about 0.1 wt % to about 10 wt % of the sunscreen formulation. The balance comprises a cosmetically or pharmaceutically acceptable carrier.

The sunscreen formulations may contain dispersing agents, emulsifiers or thickening agents to assist in applying a uniform layer of the active compounds. Suitable dispersing agents for the sunscreen formulations include those useful for dispersing organic or inorganic sunscreen agents in either a water phase, an oil phase, or part of an emulsion, including, for example, chitosan.

Emulsifiers may be used in the sunscreen formulations to disperse one or more of the compounds of formulae I-VI or other component of the sunscreen formulation. Suitable emulsifiers include conventional agents such as, for example, glycerol stearate, stearyl alcohol, cetyl alcohol, dimethicone copolyol phosphate, hexadecyl-D-glucoside, octadecyl-D-glucoside, etc.

Thickening agents may be used to increase the viscosity of the sunscreen formulations. Suitable thickening agents include carbomers, acrylate/acrylonitrile copolymers, xanthan gum and combinations of these. The carbomer thickeners include the crosslinked CARBOPOL acrylic polymers from B.F. Goodrich. The amount of thickener within the sunscreen formulation, on a solids basis without water, may range from about 0.001 to about 5%, preferably from 0.01 to about 1% and optimally from about 0.1 to about 0.5% by weight.

Minor optional adjunct ingredients for the sunscreen formulations to be applied to skin or hair may include preservatives, waterproofing agents, fragrances, anti-foam agents, plant extracts (Aloe vera, witch hazel, cucumber, etc) opacifiers, skin conditioning agents and colorants, each in amounts effective to accomplish their respective functions.

The sunscreen formulations may optionally contain an ingredient which enhances the waterproof properties such as, compounds that form a polymeric film, such as dimethicone copolyol phosphate, diisostearoyl trimethyolpropane siloxysilicate, chitosan, dimethicone, polyethylene, polyvinylpyrrolidone/vinylacetate, PVP/Eiconsene copolymer and adipic acids/diethylene glycol/glycerine crosspolymer etc. Waterproofing agents may be present at levels of from about 0.01 to about 10% by weight.

The sunscreen formulations may also optionally contain one or more skin conditioning agents. These include humectants, exfoliants and emollients.

Humectants are polyhydric alcohols intended for moisturizing, reducing scaling and stimulating the removal of built scale from the skin. Typically polyhydric alcohols include polyalkylene glycols and more preferably allylene polyols and their derivatives. Illustrative are propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2, 6-hexanetriol, glycerin, ethoxylated glycerin, propoxylated glycerin and mixtures thereof. Most preferably the humectant is glycerin. Amounts of humectant can range anywhere from 1 to 30%, preferably from 2 to 20% and optimally from about 5 to 10% by weight of the sunscreen composition or capsule.

The exfoliants suitable for use in the present may be selected from alpha-hydroxy carboxylic acids, beta hydroxy-carboxylic acids and salts of these acids. Most preferred are glycolic, lactic and salicylic acids and their alkali, metal or ammonium salts.

Suitable emollients include those agents known for softening the skin or hair, which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Ester emollients may be those selected from one or more of the following, triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylic/capric glycerides, propylene glycol dicaprylate/dicaprate and decyl oleate.

The sunscreen formulations may optionally contain one or more inorganic sunscreen agents as discussed above including micro fine surface treated titanium dioxide and micro fine untreated and surface treated zinc oxide. Titanium dioxide in the sunscreen compositions or capsules preferably has a mean primary particle size of between 5 and 150 nm and preferably from 10 to 100 nm. Titanium oxide may have anatase, rutile or amorphous structure. The zinc oxide in the sunscreen compositions or capsules preferably has a mean primary particle size of between 5 nm and 150 nm, preferably between 10 nm and 100 nm. Examples of modified titanium dioxide compositions include:

Eusolex® T-45D (surface treated with alumina and simethicone, 45% dispersion in isononoyl isononoate);

Eusolex® T-Aqua, (surface treated with aluminum hydroxide, 25% dispersion in water); and Eusolex® T-2000 (surface treated with alumina and simethicone); and Eusolex® T-AVO (surface treated with silica); all available from MERCK KGaA/EMD Chemicals.

The sunscreen formulation may also contain one or more additional monomeric organic chromophoric compounds. These can either be UV-A, UV-B or broad band filters. Examples of suitable UV-A sunscreens include benzophenone derivatives, menthyl anthranilate, butyl methoxydibenzoyl methane, and benzylidene-dioxoimidazoline derivatives.

UV-B organic sunscreens are preferably liquid in nature and preferably can solubilize the dibenzoylmethane derivative preferably to at least 15%. Examples of suitable UV-B sunscreens include cinnamate, salicylate and diphenylacrylate, derivatives thereof and combinations thereof. Preferred UV-B sunscreens are salicylates or cinnamates alone or in combination. Particularly, preferred UV-B organic sunscreens according to the present invention include salicylate derivatives and cinnamate derivatives.

Salicylates, such as homosalate, ethylhexyl salicylate and dipropylene glycol salicylate, are UV-B absorbers having a $\lambda_{max}$~306 nm.

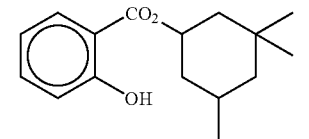

Homosalate

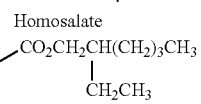

Ethylhexyl Salicylate

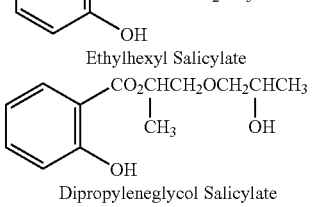

Dipropyleneglycol Salicylate

Other salicylates are also encompassed by the present invention. A composition of the invention optionally contains at least one salicylate present in an amount ranging from 0 to 80%.

Cinnamate derivatives, such as ethylhexyl methoxycinnamate (4A), isoamyl-p-methoxycinnamate (4B), cinoxate (4C), isopropyl methoxycinnamate (4D), diisopropyl methyl cinnamate (4E)) and glyceryl ethylhexanoate dimethoxycinnamate (4F), are all UV-B absorbers having a $\lambda_{max}$~310 nm.

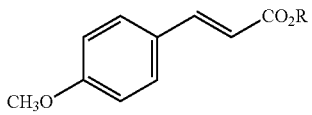

4A: Ethylhexyl Methoxycinnamate: R = 2-Ethyhexyl
4B: Isoamyl Methoxycinnamate: R = Isoamyl
4C: Cinnoxate: R = 2-Ethoxyethyl
4D: Isopropyl Methoxycinnamate: R = Isopropyl

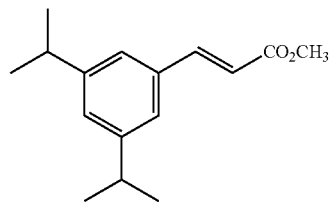

4E: Diisopropyl Methyl Cinnamate

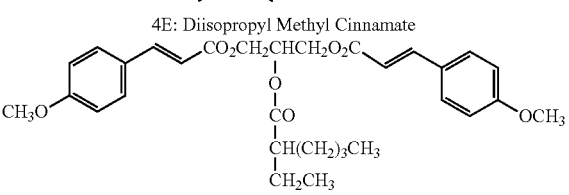

4F: Glyceryl ethylhexanoate Dimethoxycinnamate

Other cinnamates are also encompassed by the present invention. A composition of the invention optionally contains at least one cinnamate present in an amount ranging from 0 to 80%.

Examples of suitable broad-band sunscreen include benzotriazole derivatives and triazine derivatives such as anisotriazone. Others include ethylhexyltriazone and diethylhexylbutamidotriazone.

Particularly useful organic sunscreen agents that can be introduced are 2-ethylhexyl p-methoxycinnamate, 4,4'-t-butylmethoxydibenzoyl methane, 2 hydroxy-4-methoxybenzophenone, octyldimethyl p-aminobenzoic acid, 2,2-dihydroxy-4-methoxybenzophenone, ethyl-4-[bis(hydroxypropyl)]aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid, 2-ethylhexyl p-dimethylaminobenzoate, 2-phenylbenzimidazole-5-5-sulfonic acid, 2-(p-dimethylamino phenyl-5-sulfoniobenzoxazoic acid and mixtures thereof.

Examples of useful commercially available organic sunscreen agents that can be introduced include 2-phenylbenzimidazole-5-sulphonic acid, 2-(4-methylbenzylidene)-camphor, 4-isopropyldibenzoyl methane all of the Eusolex™ series sold by EMD Chemicals, Inc., USA and Merck KGaA, Darmstadt, Germany. All additional organic UV filters can optionally be used in encapsulated form, encapsulated separately or in form of mixtures. These organic UV filters are each usually incorporated into formulations in an amount of from 0.5 to 10% by weight, preferably 1-8%.

The sunscreen formulation may contain an additional antioxidant. Examples of suitable antioxidants which provide stability include p-hydroxybenzoic acid and its derivatives (ethylisobutyl, glyceryl esters of p-hydroxybenzoic acid); salicylates (octylamyl, phenyl, benzyl menthyl, glycerol and dipropyleneglycol esters); coumarin derivatives; flavones; hydroxy or methoxy substituted benzophenones; uric or tannic acid and its derivatives.

In addition to providing sunscreen activity at levels, which provide U.V. absorption, the compounds of Formula I to VI can be introduced into a skin care formulation, a hair care formulation or other personal care formulations such as cosmetic formulations at levels which provide antioxidant activity. These compounds can be used with or without conventional antioxidants in personal care formulations such as hair care, skin care and cosmetic formulations.

It has been found that to provide additional antioxidant functionality, the phenyl group of the compounds of formula I or II should have a substituent pattern of "3,5-alkoxy, 4-hydroxy" or "3-alkoxy-4-hydroxy". Compounds of formula I or II also have an extended conjugation with aromatic ring providing UV absorbing functionality, (chromophoric in the UV range). Non-aromatic functionality can vary widely in structure with examples given in formulae II, III, and IV above.

The sunscreen formulations of this invention preferably offer protection from UV radiation with wavelengths of about 290 nm to 400 nm and preferably from wavelengths in the range of about 290-370 nm. Sunscreen formulations of this invention also typically have a sunscreen protection factor (SPF) range of from about 2 to 60, with a preferred SPF range of from about 10 to about 45. The target SPF range can be achieved with a combination of both inorganic and organic chromophoric compounds. SPF is determined by techniques well known in the art, on human skin as described in the Federal Register, Aug. 25, 1978, Vol. 43, No. 166, pages 38259-38269 (Sunscreen Drug Products for Over-The-Counter Human Use, Food and Drug Administration). SPF values can also be approximated using in-vitro models as described, for example, in J. Soc. Cosmet. Chem. 44:127-133 (May/June 1989).

Compositions of this invention can be prepared as described by conventional means. A method of producing a composition for topical application by mixing sunscreen capsules as described above and a carrier suitable for topical application is a further embodiment of the present invention.

The compounds of Formula I-VI can be obtained as described in WO2003/007906A. For example preferred compounds are obtainable by condensation of a corresponding 3,5-dialkoxy,

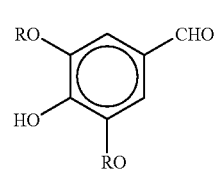

B 4-hydroxy benzaldehyde of formula B,
wherein R is as defined above, with a compound that provides the UV absorbing moiety, "A" as defined above. An example is a compound of the formula: $R_1$—$CH_2$—$C(O)XR_2$ wherein $R_1$ and $R_2$ and X are as defined above.

The benzaldehyde of formula B can be obtained commercially or prepared from 3,4,5-trimethoxybenzaldehyde through selective monodemethylation at the 4-position. Alternately, syringaldehyde can be prepared from 3-methoxy-4-hydroxy-5-bromo benzaldehyde by replacing bromine with methoxy using sodium methoxide. This technique leads to syringaldehyde. The syringaldehyde is then condensed with a malonate ester or acetyl acetoacetate or similar compounds to provide the desired UV absorbing structure.

Methods of preparation of two compounds of the invention are illustrated below.

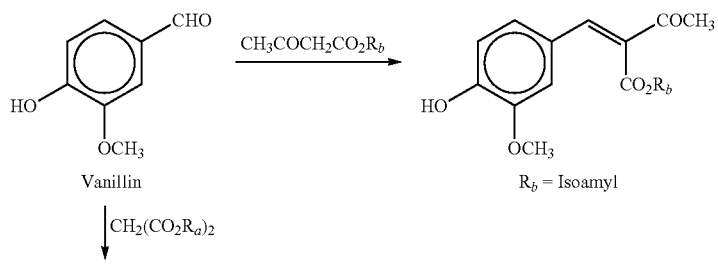

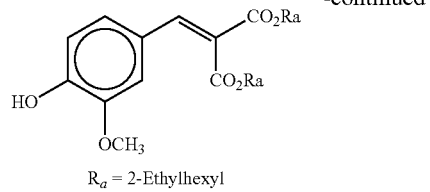

$R_a$ = 2-Ethylhexyl

In one embodiment, the invention relates to a sunscreen composition or capsule comprising i) at least one UV-A organic sunscreen and ii) at least one compound of formula VII

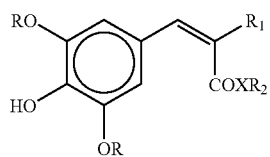

wherein each R is independently linear or branched $C_1$ to $C_8$ alkyl; $R_1$ is selected from the group consisting of —C(O)CH$_3$, —CO$_2$R$_3$, —C(O)NH$_2$, —C(O)N(R$_4$)$_2$ and —CN; X is O or NH or N—C-1-8-Alkyl, preferably N-Methyl or N-Ethyl; $R_2$ is linear or branched $C_1$ to $C_{20}$ alkyl; $R_3$ is linear or branched $C_1$ to $C_{20}$ alkyl; and each $R_4$ is independently hydrogen or linear or branched $C_1$ to $C_8$ alkyl and said composition optionally contains at least one UV-B liquid organic sunscreen and/or at least one solubilizer.

In another embodiment, $R_1$ in Formula II is selected from the group consisting —C(O)CH$_3$, —CO$_2$R$_3$, —C(O)NH$_2$ and —C(O)N(R$_4$)$_2$. In another embodiment, R is $C_1$-$C_4$ alkyl, X is oxygen and $R_2$ is linear or branched $C_1$ to $C_4$ alkyl. In yet another embodiment, $R_1$ is CO$_2$R$_3$ and $R_3$ is linear or branched $C_1$ to $C_4$ alkyl. In another embodiment, $R_1$ is C(O)CH$_3$. In yet another embodiment $R_1$ is —C(O)N(R$_4$)$_2$, and at least one $R_4$ is hydrogen and the other is hydrogen or linear or branched $C_1$ to $C_4$ alkyl. In another embodiment, $R_1$ is —C(O)N(R$_4$)$_2$, and each $R_4$ is independently linear or branched $C_1$ to $C_4$ alkyl. In yet another embodiment, R is $C_1$-$C_4$ alkyl, $R_1$ is —CO$_2$R$_3$, and at least one of $R_2$ and $R_3$ is linear or branched $C_8$ to $C_{20}$ alkyl. In another embodiment, $R_2$ and $R_3$ are each linear or branched $C_8$ alkyl. In yet another embodiment, at least one of $R_2$ and $R_3$ is linear or branched $C_{12}$ to $C_{20}$ alkyl. In another embodiment, R is methyl or ethyl.

In another embodiment, the UV-A organic sunscreen is 4-(tert-butyl)-4'-methoxydibenzoylmethane and said compound of formula II is di-2-ethylhexyl-3,5-dimethoxy-4-hydroxy-benzalmalonate.

In another embodiment, the 4-(tert-butyl)-4'-methoxydibenzoylmethane and di-2-ethylhexyl-3,5-dimethoxy-4-hydroxy-benzalmalonate are present in a weight-ratio from about 3:1 to about 1:3, preferably from about 1:0.8 to 1:2.

In yet another embodiment, the capsule contains 4-(tert-butyl)-4'-methoxydibenzoylmethane and said compound of formula II is di-2-ethylhexyl-3,5-dimethoxy-4-hydroxy-benzalmalonate and Homosalate.

In another embodiment, the UV-A organic sunscreen is 4-(tert-butyl)-4'-methoxydibenzoylmethane and said compound of formula II is di-2-ethylhexyl-3,5-dimethoxy-4-hydroxy-benzalmalonate. In another embodiment, the 4-(tert-butyl)-4'-methoxydibenzoylmethane and di-2-ethylhexyl-3,5-dimethoxy-4-hydroxy-benzalmalonate are in a ratio of 1:2 or 1:3.

In yet another embodiment, the capsule contains 4-(tert-butyl)-4'-methoxydibenzoylmethane, di-2-ethylhexyl-3,5-dimethoxy-4-hydroxy-benzalmalonate and Octyl methoxy cinnamate (Octinoxate).

In another embodiment, the sunscreen composition or capsule comprises i) at least one UV-A organic sunscreen and ii) at least one compound of formula III or IV

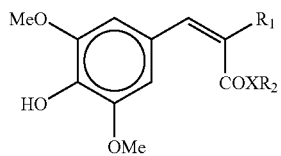

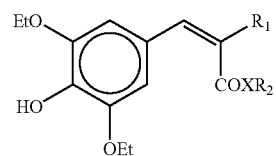

wherein $R_1$ is selected from the group consisting —C(O)CH$_3$, —CO$_2$ ($C_1$-$C_8$ alkyl), —C(O)NH$_2$, —C(O)N($C_1$-$C_4$ alkyl)$_2$ and —CN; X is O or NH or N—C1-8-Alkyl; and $R_2$ is $C_1$-$C_{12}$ alkyl and said composition optionally contains at least one UV-B liquid organic sunscreen and/or at least one solubilizer.

In another embodiment, $R_1$ of formula III or IV is selected from the group consisting —C(O)CH$_3$, —CO$_2$ ($C_1$-$C_8$ alkyl), —C(O)NH$_2$, —C(O)NH($C_1$-$C_4$ alkyl), and —C(O)N($C_1$-$C_4$ alkyl)$_2$. In another embodiment, X is oxygen and $R_2$ is linear or branched $C_1$ to $C_4$ alkyl and $R_1$ is selected from the group consisting of —CO$_2$($C_1$-$C_4$ alkyl); —C(O)NH($C_1$-$C_4$ alkyl), —C(O)CH$_3$, —C(O)NH$_2$, and —C(O)N($C_1$-$C_4$ alkyl)$_2$. In yet another embodiment, $R_1$ is —CO$_2$C$_8$H$_{18}$.

In another embodiment, the compound of formula II is selected from the group consisting of ethyl-alpha-acetyl-3,5-dimethoxy-4-hydroxy cinnamate; iso-propyl-alpha-acetyl-3,5-dimethoxy-4-hydroxy cinnamate; iso-amyl-alpha-acetyl-3,5-dimethoxy-4-hydroxy cinnamate; 2-ethylhexyl-alpha-acetyl-3,5-dimethoxy-4-hydroxy cinnamate; diethyl-3,5-dimethoxy-4-hydroxy benzylidene malonate; di-(2-ethylhexyl)-3,5-dimethoxy-4-hydroxy benzylidene malonate; diisoamyl-3,5-dimethoxy-4-hydroxy benzylidene malonate; dipalmitoyl-3,5-dimethoxy-4-hydroxy benzylidene malonate; di-dodecyl-3,5-dimethoxy-4-hydroxy benzylidene malonate; and di-isopropyl-3,5-dimethoxy-4-hydroxy benzylidene malonate.

In another embodiment, the compound of formula II is present in an amount effective to adsorb illumination in a range from 290 to 400, preferably above 320 nm wavelength.

In one embodiment, the sunscreen composition or capsule comprises from 0.1 to 40 wt % of a compound of formula II, and optionally contains an additional organic sunscreen agent for filtering UV-B rays, UV-A rays or both, said agent may be an inorganic metal oxide sunscreen agent. Preferably, the compound of Formula II stabilizes the additional sunscreen agent against degradation from exposure to light.

In another embodiment, the present invention relates to a method of protecting a substrate from UV radiation comprising applying a sunscreen composition or capsule or personal care composition of the invention to said substrate, e.g., skin or hair.

In another embodiment, the present invention relates to a sunscreen composition or capsule comprising i) at least one UV-A organic sunscreen and at least one compound selected from the group consisting of ethyl-alpha-acetyl-3,5-dimethoxy-4-hydroxy cinnamate; iso-propyl-alpha-acetyl-3,5-dimethoxy-4-hydroxy cinnamate; iso-amyl-alpha-acetyl-3,5-dimethoxy-4-hydroxy cinnamate; 2-ethylhexyl-alpha-acetyl-3,5-dimethoxy-4-hydroxy cinnamate; diethyl-3,5-dimethoxy-4-hydroxy benzylidene malonate; di-(2-ethylhexyl)-3,5-dimethoxy-4-hydroxy benzylidene malonate; diisoamyl-3,5-dimethoxy-4-hydroxy benzylidene malonate; dipalmitoyl-3,5-dimethoxy-4-hydroxy benzylidene malonate; di-dodecyl-3,5-dimethoxy-4-hydroxy benzylidene malonate; and di-isopropyl-3,5-dimethoxy-4-hydroxy benzylidene malonate. The sunscreen may further comprise at least one UV-B liquid organic sunscreen and/or at least one solubilizer, and is preferably prepared by sol gel encapsulation.

In another embodiment, the sunscreen composition or capsule further comprising an antioxidant other than a compound of formula II. The antioxidant may be, for example, a Tocopherol, tocopherylacetate, Ascorbic acid, Emblica antioxidants, Proanthocyanidins, Rosemary antioxidants, green tea polyphenols, gallic acid, ellagic acid, butylhydroxy toluene (BHT) and butylhydroxy anisole (BHA).

In another embodiment the compound of formula I or II is selected from the group consisting of ethyl-alpha-cyano-3-methoxy-4-hydroxy cinnamate; ethyl-alpha-acetyl-3-methoxy-4-hydroxy cinnamate; iso-propyl-alpha-acetyl-3-methoxy-4-hydroxy cinnamate; iso-amyl-alpha-acetyl-3-methoxy-4-hydroxy cinnamate; 2-ethylhexyl-alpha-acetyl-3-methoxy-4-hydroxy cinnamate; diethyl-3-methoxy-4-hydroxy benzylidene malonate; di-(2-ethylhexyl)-3-methoxy-4-hydroxy benzylidene malonate; diisoamyl-3-methoxy-4-hydroxy benzylidene malonate; dipalmitoyl-3-methoxy-4-hydroxy benzylidene malonate; di-dodecyl-3-methoxy-4-hydroxy benzylidene malonate; di-isopropyl-3-methoxy-4-hydroxy benzylidene malonate; di-(2-ethyhexyl)-3-methoxy-4-hydroxy-5-isopropyl-benzylidene malonate; di-isoamyl-3-methoxy-4-hydroxy-5-tert.butyl-benzylidene malonate; iso-amyl-alpha-acetyl-3-methoxy-4-hydroxy-5-isopropyl cinnamate; and iso-amyl-alpha-acetyl-3-methoxy-4-hydroxy-5-tert.butyl cinnamate.

In another embodiment, the compound of formula I or II is present in an amount effective to adsorb illumination in a range from 290 to 400, preferably above 320 nm wavelength.

In one embodiment, the sunscreen composition or capsule comprises from 0.1 to 40 wt. % of a compound of formula I or II, and optionally contains an additional organic sunscreen agent for filtering UV-B rays, UV-A rays or both, said agent may be an inorganic metal oxide sunscreen agent. Preferably, the compound of Formula I or II stabilizes the additional sunscreen agent against degradation from exposure to light.

A composition for topical application that comprises i) at least one capsule as described above and ii) a carrier suitable for topical application is a further embodiment of the present invention.

Preferably the composition for topical application comprises additionally iii) at least one adjuvant selected from the group consisting of preservatives, antifoams, perfumes, oils, waxes, propellants, dyes, pigments, waterproofing agents, emulsifiers, surfactants, thickeners, humectants, exfoliants and emollients.

The composition for topical application is preferably in a form selected from the group consisting of creams, ointments, suspensions, powders, oily lotions, oleo-alcoholic lotions, fatty gels, oleo-alcoholic gels, solid sticks, foams, emulsions, liquid dispersions, sprays, aerosols, lipsticks, foundation, make-up, loose or press powder, eye blush, eye shadows or nail lacquer.

The composition for topical application preferably comprises at least one additional organic sunscreen agent for filtering UV-B rays, UV-A rays or both, wherein preferably the at least one additional organic sunscreen agent for filtering UV-B rays, UV-A rays or both is encapsulated.

In another embodiment the composition for topical application comprises at least one additional antioxidant, preferably selected from the group consisting of Tocopherols, tocopherylacetate, Ascorbic acid, Emblica antioxidants, Proanthocyanidins, Rosemary antioxidants, green tea polyphenols, gallic acid, ellagic acid, butylhydroxy toluene (BHT) and butylhydroxy anisole (BHA).

In yet another embodiment, the sunscreen composition or capsule is free of photostabilizers other than compounds of formula V, which is present in an amount within the range of 0.1% to 40 wt % of said sunscreen formulation.

In another embodiment, the sunscreen composition or capsule comprises an antioxidant other than a compound of formula V, said additional antioxidant may be, for example, Tocopherols, tocopherylacetate, Ascorbic acid, Emblica antioxidants, Proanthocyanidins, Rosemary antioxidants, green tea polyphenols, gallic acid, ellagic acid, butylhydroxy toluene (BHT) and butylhydroxy anisole (BHA).

In yet another embodiment, the compound of formula V is present in an amount effective to protect formulation ingredients from oxidation.

In yet another embodiment, the present invention relates to a method of protecting a substrate from UV radiation which comprises applying a sunscreen composition or capsule as described above to said substrate.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The entire disclosure of all applications, patents and publications, cited herein and the disclosure of the priority document are hereby incorporated by reference. The following examples have not all necessarily been actually conducted.

EXAMPLES

A. Preparation of Photostabilizers

Example I

2-Ethylhexyl-alpha-aceto-3,5-dimethoxy-4-hydroxy cinnamate

Monodemethylation of 3,4,5-trimethoxy benzaldehyde using sulphuric acid at 40° C. for 8 hours yields 3,5-

Dimethoxy-4-hydroxy benzaldehyde (Syringaldehyde). Condensation of syringaldehyde with 2-ethylhexyl acetoacetate in the presence of piperidine—acetic acid and benzene as the reaction medium at reflux temperature under continuous azeotropic water removal yields the title product. The reaction takes about 1.5 hours for completion. The yield obtained is typically 92%.

Example II

Diethyl-3,5-dimethoxy-4-hydroxy benzylidene malonate

Monodemethylation of 3,4,5-trimethoxy benzaldehyde using sulphuric acid at 40° C. for 8 hours as described above in Example 1 yields syringaldehyde.

Condensation of 3,5-Dimethoxy-4-hydroxy benzaldehyde (Syringaldehyde) with diethyl malonate in the presence of piperidine—acetic acid and benzene as the reaction medium at reflux temperature under continuous azeotropic water removal yields the title product. The reaction takes about 7.5 hours for completion.

Example III

Ethyl-alpha-methyl-3,5-dimethoxy-4-hydroxy cinnamate

Monodemethylation of 3,4,5,-trimethoxybenzaldehyde using sulphuric acid at 40° C. for 8 hours as described above in Example 1 yields syringaldehyde.

The Wittig salt is prepared by reaction of triphenyl phosphine and ethyl-2-bromopropionate in benzene media at 70-75EC for 8 hours and subsequent basification with 1N Sodium hydroxide to phenolphthalein end point at room temperature. Extraction with benzene, concentration of the benzene extract and the addition of petroleum ether (60-80° C.) yield triphenyl methyl carbethoxy methylene phosphorane as a solid product.

Condensation of 3,5-Dimethoxy-4-hydroxybenzaldehyde (Syringaldehyde) with triphenyl methyl carbethoxy methylene phosphorane is performed at reflux temperature in xylene for seven hours and after work up, yields the title compound.

Example IV

Ethyl-alpha-acetyl-3,5-dimethoxy-4-hydroxy-cinnamate

Monodemethylation of 3,4,5-trimethoxy benzaldehyde using sulphuric acid at 40° C. for 8 hours as described above in Example 1 yields syringaldehyde.

Condensation of 3,5-Dimethoxy-4-hydroxy benzaldehyde (syringaldehyde) with ethyl acetoacetate in the presence of piperidine—acetic acid and benzene as the reaction medium at reflux temperature yields the title product. The reaction takes about 3.5 hours for completion.

Example V

Di-(2-Ethylhexyl)-3,5-dimethoxy-4-hydroxy benzylidene malonate

Monodemethylation of 3,4,5-trimethoxy benzaldehyde using sulphuric acid at 40° C. for 8 hours as described above in Example 1 yields syringaldehyde.

Transesterfication of diethyl malonate using 2-ethylhexyl alcohol in neat condition at 140-155° C. for 2 hours under nitrogen blanketing in the presence of sulphuric acid and after work up, followed by high vacuum distillation, yields di-6-ethylhexyl malonate.

Condensation of 3,5-Dimethoxy-4-hydroxy benzaldehyde (Syringaldehyde) with di-2-ethylhexyl malonate in the presence of piperidine—acetic acid and benzene as the reaction medium at reflux temperature under continuous azeotropic water removal yields di-2-ethylhexyl-3,5-dimethoxy-4-hydroxy benzylidene malonate. The reaction takes about nine hours for completion. The yield typically obtained is 91%.

Example VI

Di-isoamyl-3,5-dimethoxy-4-hydroxy benzylidene malonate

Example V was repeated, except in the condensation step, di-2-ethyhexyl malonate was replaced with di-isoamyl malonate. The yield typically obtained was over 90%.

Example VII

Di-isopropyl-3,5-dimethoxy-4-hydroxy benzylidene malonate

Example V was repeated, except in the condensation step, di-2-ethyhexyl malonate was replaced with di-isopropyl malonate. The yield typically obtained was over 90%.

Example VIII

Di-dodecyl-3,5-dimethoxy-4-hydroxy benzylidene malonate

Example V was repeated, except in the condensation step, di-2-ethyhexyl malonate was replaced with di-dodecyl malonate. The yield typically obtained was over 90%.

Example IX

Iso-propyl-alpha-acetyl-3,5-dimethoxy-4-hydroxy-cinnamate

Example IV was repeated, except in the condensation step, ethyl acetoacetate was replaced with iso-propyl acetoacetate. The yield of the desired product was 88%.

Example X

Iso-butyl-alpha-acetyl-3,5-dimethoxy-4-hydroxy-cinnamate

Example IV was repeated, except in the condensation step, ethylacetoacetate was replaced with iso-butyl-acetoacetate. The yield of the desired product was 89%.

Example XI

Iso-amyl-alpha-acetyl-3,5-dimethoxy-4-hydroxy-cinnamate

Example IV was repeated, except in the condensation step, ethylacetoacetate was replaced with iso-amyl acetoacetate. The yield of the desired product was 89%.

Example XII

Ethyl-alpha-cyano-3-methoxy-4-hydroxy cinnamate

Condensation of vanillin with ethyl cyanoacetate in the presence of piperidine—acetic acid and benzene as the reaction medium at reflux temperature under continuous azeotropic water removal yields the title product. The reaction takes about 1.5 hours for completion. The yield obtained is typically 95%.

Example XIII

Diethyl-3-methoxy-4-hydroxy benzylidene malonate

Condensation of 3-methoxy-4-hydroxy benzaldehyde (vanillin) with diethyl malonate in the presence of piperidine—acetic acid and benzene as the reaction medium at reflux temperature under continuous azeotropic water removal yields the title product. The reaction takes about 6.5 hours for completion.

Example XIV

Ethyl-alpha-acetyl-3-methoxy-4-hydroxy-cinnamate

Condensation of 3-methoxy-4-hydroxy benzaldehyde (vanillin) with ethyl acetoacetate in the presence of piperidine—acetic acid and benzene as the reaction medium at reflux temperature yields the title product. The reaction takes about 3.5 hours for completion.

Example XV

Di-(2-Ethylhexyl)-3-methoxy-4-hydroxy benzylidene malonate

Transesterification of diethyl malonate using 2-ethylhexyl alcohol in neat condition at 140-155EC for 2 hours under nitrogen blanketing in the presence of sulfuric acid and after work up, followed by high vacuum distillation, yields di-6-ethylhexyl malonate.

Condensation of 3-methoxy-4-hydroxy benzaldehyde (vanillin) with di-2-ethylhexyl malonate in the presence of piperidine—acetic acid and benzene as the reaction medium at reflux temperature under continuous azeotropic water removal yields di-2-ethylhexyl-3-methoxy-4-hydroxy benzylidene malonate. The reaction takes about nine hours for completion. The yield typically obtained is 91%.

Example XVI

Di-isoamyl-3-methoxy-4-hydroxy benzylidene malonate

Example IV is repeated, except in the condensation step, di-2-ethyhexyl malonate is replaced with di-isoamyl malonate. The yield typically obtained is over 90%.

Example XVII

Di-isopropyl-3-ethoxy-4-hydroxy benzylidene malonate

Example IV is repeated, except in the condensation step, di-2-ethyhexyl malonate is replaced with di-isopropyl malonate. The yield typically obtained is over 90%.

Example XVIII

Di-dodecyl-3-methoxy-4-hydroxy benzylidene malonate

Example IV is repeated, except in the condensation step, di-2-ethyhexyl malonate is replaced with di-dodecyl malonate. The yield typically obtained is over 90%.

Example XIX

Iso-propyl-alpha-acetyl-3-methoxy-4-hydroxy-cinnamate

Example III is repeated, except in the condensation step, ethyl acetoacetate is replaced with iso-propyl acetoacetate. The yield of the desired product is 88%.

Example XX

Iso-butyl-alpha-acetyl-3-methoxy-4-hydroxy-cinnamate

Example III is repeated, except in the condensation step, ethylacetoacetate is replaced with iso-butyl-acetoacetate. The yield of the desired product is 89%.

Example XXI

Iso-amyl-alpha-acetyl-3-methoxy-4-hydroxy-cinnamate

Example III is repeated, except in the condensation step, ethylacetoacetate is replaced with iso-amyl acetoacetate. The yield of the desired product is 89%.

Example XXII

Disoamyl-3-methoxy-4-hydroxy-5-isopropyl benzylidene malonate

Condensation of 3-methoxy-4-hydroxy-5-isopropyl benzaldehyde with di-isoamyl malonate in the presence of piperidine-acetic acid and benzene as the reaction medium at reflux temperature under continuous azeotropic water removal yields the title product. The reaction takes about 3 hours for completion. The yield obtained is typically 90-95%.

Example XXIII

Isoamyl-alpha-acetyl-3-methoxy-4-hydroxy-5-isopropyl-cinnamate

Condensation of 3-methoxy-4-hydroxy-5-isopropyl benzaldehyde with isoamyl acetoacetate in the presence of piperidine-acetic acid and benzene as the reaction medium at reflux temperature under continuous azeotropic water removal yields the title product. The reaction takes about 4 hrs for completion. The yield obtained is typically 90-95%.

B. Preparation of Co-Encapsulated Materials

Example 1A

Co-encapsulation of Homomethyl salicylate (Homosalate, HMS), Butyl Methoxydibenzoylmethane (Avobenzone, BMDBM) and Diethylhexyl 3,5-dimethoxy-4-hydroxy benzylidene malonate (Oxynex ST)

10 g BMDBM is dissolved in 30 g HMS and 10 g Oxynex ST. The obtained mixture is dissolved in 51.4 g of tetraethoxysilane (TEOS) and the organic phase is emulsified in 240 g of aqueous solution containing 1% cetyltrimethyl ammonium chloride (CTAC) under high shear forces using an Ultra-Turrax T-25 basic with S 25 KR-18G dispersing tool (IKA) at 19,000 rpm. The vessel walls are cooled by immersion in an ice-water bath during the homogenizing process. Obtained emulsion is then poured in to an IKA LR-A 1000 Laboratory reactor, equipped with Eurostar Power control-visc P4 stirrer, containing 350 NaOH aqueous solution at pH 11.3. The emulsion is stirred at room temperature for 24 hours. The product is precipitated in a centrifuge at 20,000 g, rinsed by re-suspending in deionized water, precipitated again and finally re-suspended in a 1% polyvinyl pyrrolidone (PVP K30, ISP) to afford a stable dispersion containing 21.4% HMS, 7.5% BMDBM and 7.8% Oxynex ST in the suspension.

The obtained suspension has particle size D-90 of 1.828, is smooth, pleasant to touch and can be incorporated into various cosmetic vehicles to obtain a sunscreen composition or capsule useful for protecting skin against ultraviolet radiation.

Example 2A

Co-encapsulation of Homosalate (HMS), Butyl Methoxydibenzoylmethane (Avobenzone) and Diethylhexyl 3,5-dimethoxy-4-hydroxy benzylidene malonate (Oxynex ST)

Example 1A is repeated, except the amount of Diethylhexyl 3,5-dimethoxy-4-hydroxy benzylidene malonate (Oxynex ST) is increased to 15 g and the amount of HMS is decreased to 25 g. Usual processing as described above afforded a stable dispersion containing 18.2% HMS, 7.4% BMDBM and 12.1% Oxynex ST in the suspension.

Example 3A

Co-encapsulation of Homosalate (HMS), Butyl Methoxydibenzoylmethane (Avobenzone) and Isoamyl-α-acetyl-3,5-dimethoxy-4-hydroxy cinnamate Example 1A is repeated, except isoamyl-α-acetyl-3,5-dimethoxy-4-hydroxy cinnamate is used instead of Diethylhexyl 3,5-dimethoxy-4-hydroxy benzylidene malonate.

Example 4A

Co-encapsulation of Octyl salicylate, Butyl Methoxydibenzoylmethane (Avobenzone) and Diethylhexyl-3,5-dimethoxy-4-hydroxy benzylidene malonate Example 1A is repeated, except homomethyl salicylate is replaced with Octyl salicylate.

Example 5A

Co-encapsulation of Caprylic/Capric Triglyceride, Butyl Methoxydibenzoylmethane (Avobenzone) and Diethylhexyl-3,5-dimethoxy-4-hydroxy benzylidene malonate Example 1A is repeated, except homomethyl salicylate is replaced with Caprylic/Capric Triglyceride.

Example 6A

Co-encapsulation of Homosalate (HMS), Butyl Methoxydibenzoylmethane (Avobenzone) and Diethylhexyl 3,5-dimethoxy-4-hydroxy benzylidene malonate (Oxynex ST) having a capsule wall made of organopolysiloxane composed of a co-polycondensate of the hydrolysate of methoxy (ethoxy) n-propyldihydroxymethylsilane, methyltriethoxysilane and phenyltriethoxysilane.

a) Preparation of Prepolymer of Capsule Wall

A 2-liter round bottom cylindrical glass reaction vessel having an internal diameter of 12 cm equipped with a mechanical stirrer, having an upper cover equipped with a dropping funnel and a reflux condenser, is previously charged 90 g of water, 10 g of a polyoxyethylene-modified silicone (KF-354A (trade name) manufactured by Shin-Etsu Silicone Co., Ltd., and produced by substituting both ends of methoxy (ethoxy) n-propyldihydroxymethylsilane with trimethyl silyl groups.) and 0.2 g of 18% hydrochloric acid. A mixture of 4.4 g of methyltriethoxysilane and 1.2 g of phenyltriethoxysilane is added dropwise from the dropping funnel at 50° C. with stirring. The mixture is further stirred for 6 hours at 50° C., then, 1.6 g of 4% aqueous sodium hydroxide solution is added dropwise with stirring to control the pH to 7.0. Thereafter, the mixture is stirred for 1 hour at 50° C.

b) Addition of Core Material and Emulsification 5.0 g of a mixture of Homosalate (HMS), Butyl Methoxydibenzoylmethane (BMDBM) and Diethylhexyl 3,5-dimethoxy-4-hydroxy benzylidene malonate (3:1:1 w/w ratio) are added to the reaction solution prepared in the process 1) with stirring at 600 rpm, and the mixture is further stirred for 4 hours at 600 rpm.

c) Prevention of Coagulation and Curing Treatment of Capsule Wall 0.5 g of trimethylchlorosilane is added to the solution prepared in the process 2) in a reaction vessel with stirring at 600 rpm and 50° C., then, immediately, 1 g of a 20% aqueous sodium hydroxide solution is added dropwise. The temperature of the reaction solution is raised gradually to reflux. A vapor containing alcohol is distilled off, and the remaining mixture is further heated to reflux with stirring at 150 rpm for 6 hours. This reaction solution is cooled with stirring at 150 rpm at room temperature to obtain a microcapsule containing a core material.

Example 7A

Co-encapsulation of Homosalate (HMS), Butyl Methoxydibenzoylmethane (Avobenzone) and Diethylhexyl 3-methoxy-4-hydroxy benzylidene malonate having a capsule wall made of organopolysiloxane composed of a co-polycondensate of the hydrolysate of methoxy (ethoxy) n-propyldihydroxymethylsilane, methyltriethoxysilane and phenyltriethoxysilane.

Example 7A is repeated except Diethylhexyl-3,5-dimethoxy-4-hydroxybenzylidene malonate is replaced with Diethylhexyl 3-methoxy-4-hydroxy benzylidene malonate

Example 8A

Co-encapsulation of caprylic/capric triglyceride, Butyl Methoxydibenzoylmethane (Avobenzone) and Diethylhexyl 3-methoxy-4-hydroxy benzylidene malonate having a capsule wall made of organopolysiloxane composed of a co-polycondensate of the hydrolysate of methoxy (ethoxy) n-propyldihydroxymethylsilane, methyltriethoxysilane and phenyltriethoxysilane.

Example 6A is repeated except homosalate is replaced with caprylic/capric triglycerides

C. Formulations of Co-Encapsulated Materials

Example-1B

Sunscreen Lotion Using Co-Encapsulated Material from Example-1A

| INCI name | Trade Name/Supplier | % w/w |
|---|---|---|
| Phase A | | |
| Water (demineralized) | | qs |
| Disodium EDTA | | 0.10 |
| Glycerin | | 2.00 |
| Propylene Glycol | | 3.00 |
| Phase B | | |
| Xanthan gum | Vanzan NF/Vanderbilt | 0.20 |
| Phase C | | |
| Glyceryl Stearate, PEG-100 Stearate | Arlacel 165/Uniquema | 2.00 |
| Glyceryl Stearate | Cerasynt GMS/ISP | 1.50 |
| Stearic acid | Emery 132/Cognis | 1.00 |
| Cetyl Alcohol | Crodacol C-70/Croda | 1.00 |
| C12-15 Alkyl benzoate | Finsolv TN/Finetex | 8.00 |
| Dimethicone | DC 200, 10 cst/Dow Corning | 1.00 |
| PVP/Eicosene Copolymer | Ganex V220/ISP | 0.75 |
| Phase D | | |
| Phenoxyethanol, butylparaben, ethylparaben, propylparaben and methylparaben | Phenonip/ISP | 1.00 |
| Phase E | | |
| Co-encapsulated materials of Butyl methoxydibenzoymethane, Diethylhexyl-3,5-dimethoxy-4-hydroxy benzylidene malonate & HMS | Present Invention/Example 1A | 20.00 |
| Triethanolamine (99%) | TEA 99%/Union Carbide | 0.08 |
| Total | | 100.000 |

Procedure:

Combine A and heat to 70-75° C. Disperse B in A under agitation.

Combine C and heat to 70-75° C. Add C to phase A/B under agitation.

Homogenize mixture. Allow to cool while mixing. Add D at 40 C.

Add E at 40° C. Mix until mixture reaches RT.

Example-2B

Sunscreen Lotion Using Co-Encapsulated Material from Example-1A

| INCI name | Trade Name/Supplier | % w/w |
|---|---|---|
| Phase A-1 | | |
| Deionized water | | qs |
| Disodium EDTA | | 0.05 |
| Proylene Glycol | | 3.00 |
| Glycerin | | 2.00 |
| Phase A-2 | | |
| Acrylates/C10-30 Alkyl Acrylate Copolymer | Carbopol EDT 2020/Goodrich | 0.08 |
| Xanthan Gum | Vanzan NF/Vanderbilt | 0.10 |
| Phase B | | |
| Cetyl alcohol, glyceryl stearate, PEG-75, ceteth-20 and steareth-20 | Emolium Delta/Gattefosse | 3.50 |
| Dimethicone | DC200 fluid, 10 cst | 0.50 |
| C30-38 Olefin/Isopropyl Maleate/MA Copolymer | Performa V1608/New Phase Technologies | 0.75 |
| C12-15 Alkyl benzoate | Finsolv TN/Finetex | 6.00 |
| Caprylic/capric triglyceride | Myritol 318/Cognis | 14.00 |
| Phase C | | |
| Phenoxyethanol (and) Isopropylparaben (and) Isobutylparaben (and) Butylparaben | Liquapar PE/Sutton | 1.00 |
| Phase D | | |
| Co-encapsulated materials of Butyl methoxydibenzoymethane, Diethylhexyl-3,5-dimethoxy-4-hydroxy benzylidene malonate & HMS | Present Invention/Example 1A | 10.00 |
| Triethanolamine (99%) | TEA 99%/Union Carbide | 0.08 |
| Total | | 100.00 |

Procedure:

Disperse A-2 in A-1 under agitation. Heat A to 70-75° C.

Combine Phase B ingredients. Stir and heat to 70-75° C.

Add Phase B to Phase A while stirring.

Add phase C. Homogenize until mixture cools to 45-40° C.

Add Phase D. Stir allowing mixture to cool to RT.

Example-3B

Sunscreen Lotion Co-Encapsulated Materials with DHA

| INCI name | Trade Name/Supplier | % w/w |
|---|---|---|
| Phase A-1 | | |
| Deionized water | | qs |
| Disodium EDTA | | 0.10 |
| Proylene Glycol | | 3.00 |
| Glycerin | | 2.00 |
| Phase A-2 | | |
| Xanthan Gum | Vanzan NF/Vanderbilt | 0.25 |
| Phase B | | |
| Cetyl alcohol, glyceryl stearate, PEG-75, ceteth-20 and steareth-20 | Emolium Delta/Gattefosse | |
| PEG-100 Stearate, Glyceryl Stearate | Arlacel 165/Uniquema | 3.00 |
| Cetearyl Glucoside, Cetearyl Alcohol | Montanov 68/Seppic | 2.00 |
| Dimethicone | DC200 fluid, 100 cst | 1.00 |
| C30-38 Olefin/Isopropyl Maleate/MA Copolymer | Performa V1608/New Phase Technologies | 1.00 |
| C12-15 Alkyl benzoate | Finsolv TN/Finetex | 6.00 |
| Phase C | | |
| Phenoxyethanol (and) Isopropylparaben (and) Isobutylparaben (and) Butylparaben | Liquapar PE/Sutton | 1.00 |
| Phase D | | |
| Co-encapsulated materials of Butyl methoxydibenzoymethane, Diethylhexyl-3,5-dimethoxy-4-hydroxy benzylidene malonate & HMS | Present Invention/Example 1A | 15.00 |
| Triethanolamine (99%) | TEA 99%/Union Carbide | 0.08 |
| Phase E | | |
| Water | | 10.00 |
| DHA | | 6.00 |
| Total | | 100.00 |

Procedure:
Disperse A-2 in A-1 under agitation. Heat A to 70-75° C.
Combine Phase B ingredients. Stir and heat to 70-75° C.
Add Phase B to Phase A while stirring.
Add phase C. Homogenize until mixture cools to 45-40° C.
Add Phase D. Homogenize until mixture cools at around 40° C.
Add phase E. Stir allowing mixture to cool to RT

Example 4B

Sunscreen Lotion with Co-Encapsulated Materials and Insect repellents (such as IR 3535)

| INCI name | Trade Name/Supplier | % w/w |
|---|---|---|
| Phase A-1 | | |
| Deionized water | | qs |
| Disodium EDTA | | 0.10 |
| Proylene Glycol | | 2.00 |
| Glycerin | | 2.00 |
| Phase A-2 | | |
| Acrylates/C10-30 Alkyl Acrylate Copolymer | Carbopol EDT 2020/Goodrich | 0.10 |
| Xanthan Gum | Vanzan NF/Vanderbilt | 0.25 |
| Phase B | | |
| Glyceryl stearate, PEG-100 Stearate | Arlacel 165/Uniquema | 3.50 |
| Glyceryl Stearate | Cerasynt GMS/ISP | 0.50 |
| Dimethicone | DC200 fluid, 50 cst | 0.50 |
| PVP/Eicosene Copolymer | Ganex220/ISP | 1.00 |
| C12-15 Alkyl benzoate | Finsolv TN/Finetex | 6.00 |
| Cocotriglycerides | Myritol 331/Cognis | 8.00 |
| Ethyl butylacetylaminopropionate | IR3535/Rona | 10.00 |
| Stearic Acid | | 2.00 |
| Cetyl alcohol | Crodacol C-70/Croda | 1.50 |
| Phase C | | |
| Co-encapsulated materials of Butyl methoxydibenzoymethane, Diethylhexyl-3,5-dimethoxy-4-hydroxy benzylidene malonate & HMS | Present Invention/Example 1A or Example 2A | 10.00 |
| Triethanolamine (99%) | TEA 99%/Union Carbide | 0.05 |
| Phase D | | |
| Phenoxyethanol (and) Isopropylparaben (and) Isobutylparaben (and) Butylparaben | Liquapar PE/Sutton | 1.00 |
| Total | | 100.00 |

Procedure:
Disperse A-2 in A-1 under agitation. Heat A to 70-75° C.
Combine Phase B ingredients. Stir and heat to 70-75° C.
Add Phase B to Phase A while stirring.
Add phase C. Homogenize until mixture cools to 45-40° C.
Add Phase D. Stir allowing mixture to cool to RT.

Example 5B

Sunscreen Lotion with Co-Encapsulated Materials and Skin Lightening Agent

| INCI name | Trade Name/Supplier | % w/w |
|---|---|---|
| Phase A-1 | | |
| Water (demineralized) | | 67.76 |
| Disodium EDTA | | 0.05 |
| Glycerin | | 3.00 |
| Propylene Glycol | | 2.00 |
| Phase A-2 | | |
| Xantham gum | Vanzan NF/Vanderbilt | 0.25 |
| Phase B | | |
| Caprylic Capric Triglycerides | Myritol 318/Cognis | 3.50 |
| C12-15 Alkyl Benzoate | Finsolv TN/Finetex | 4.50 |
| Shea Butter | Cetiol SB-45/Cognis | 1.50 |
| Dimethicone | Dow Corning 200, 100 cst/Dow Corning | 1.00 |
| Homosalate | Eusolex HMS/Rona | 10.00 |
| Butyl methoxydibenzoylmethane | Eusolex 9020/Rona | 2.00 |
| Diethylhexyl syringylidene malonate | Oxynex ST/Rona | 2.00 |
| Glyceryl Stearate, PEG-100 Stearate | Arlacel 165/Uniqema | 3.50 |

-continued

| INCI name | Trade Name/Supplier | % w/w |
|---|---|---|
| Glyceryl Stearate | Cerasynt SD/ISP | 1.00 |
| Sorbitan Stearate | Arlacel 60/Uniquema | |
| Stearic Acid | Emersol 132/Cognis | 2.00 |
| Phase C | | |
| Water (demineralized) | | 5.00 |
| Emblica Officinallis Extract | Emblica ™/Rona | 0.50 |
| Phase D | | |
| Co-encapsulated materials of Butyl methoxydibenzoymethane, Diethylhexyl-3,5-dimethoxy-4-hydroxy benzylidene malonate & HMS | Present Invention/ Example 1A or Example 2A | 10.00 |
| Triethanolamine | | 0.15 |
| Phase E | | |
| Phenoxyethanol, Isopropyl-paraben, Isobutylparaben, Butylparaben | Liquapar PE/Sutton | 1.00 |
| Total | | 100.00 |
| | | 100.00 |

Procedure: Combine A-1; disperse A2 in A1 while stirring and heat A to 70° C.

Combine ingredients of phase B then heat to 70° C. Add phase B to A with good mixing.

Homogenize mixture at moderate speed, while cooling to 40° C. When temperature reaches 40° C. add premixed phase C; stir gently until mixture is homogeneous. Add phase D with stirring and then add phase E.

Example 6B

Sunscreen Lotion with Two Separately Prepared Co-Encapsulated Materials

| INCI name | Trade Name/Supplier | % w/w |
|---|---|---|
| Phase A | | |
| Water (demineralized) | | qs |
| Disodium EDTA | | 0.10 |
| Glycerin | | 2.00 |
| Propylene Glycol | | 3.00 |
| Phase B | | |
| Xanthan gum | Vanzan NF/Vanderbilt | 0.20 |
| Phase C | | |
| Glyceryl Stearate, PEG-100 Stearate | Arlacel 165/Uniquema | 2.00 |
| Glyceryl Stearate | Cerasynt GMS/ISP | 1.50 |
| Stearic acid | Emery 132/Cognis | 1.00 |
| Cetyl Alcohol | Crodacol C-70/Croda | 1.00 |
| C12-15 Alkyl benzoate | Finsolv TN/Finetex | 8.00 |
| Dimethicone | DC 200, 10 cst/Dow Corning | 1.00 |
| PVP/Eicosene Copolymer | Ganex V220/ISP | 0.75 |
| Phase D | | |
| Phenoxyethanol, butylparaben, ethylparaben, propylparaben and methylparaben | Phenonip/ISP | 1.00 |
| Phase E | | |
| Co-encapsulated materials of Butyl methoxydibenzoymethane, Diethylhexyl-3,5-dimethoxy-4-hydroxy benzylidene malonate, HMS | Present Invention/ Example 1A or Example 2A | 15.00 |

-continued

| INCI name | Trade Name/Supplier | % w/w |
|---|---|---|
| Encapsulated octylmethoxy cinnamate | Eusolex UV Pearl OMC/ Merck | 5.00 |
| Triethanolamine (99%) | TEA 99%/Union Carbide | 0.08 |
| Total | | 100.000 |

Procedure:

Combine A and heat to 70-75° C. Disperse B in A under agitation.

Combine C and heat to 70-75° C. Add C to phase AB under agitation.

Homogenize mixture. Allow to cool while mixing. Add D at 40 C.

Add E at 40° C. Mix until mixture reaches RT.

Example 7b

Sunscreen Lotion with Sol-Gel Capsule of Avobenzone, Octylmethoxy Cinnamate & Photostabilizer

| INCI NAME | TRADE NAME/ MANUFACTURER | % w/w |
|---|---|---|
| Phase A-1 | | |
| Water (demineralized) | q.s. | 100.00 |
| Disodium EDTA | | 0.05 |
| Butylene glycol | | 3.00 |
| Methylparaben | | 0.15 |
| Phase A-2 | | |
| Carbomer | Carbopol Ultrez 10/ Noveon | 0.20 |
| Phase B | | |
| Isopropyl myristate | Emerest 2314/Cognis | 2.50 |
| Cetyl alcohol, glyceryl stearate, PEG-75, ceteth-20 and steareth-20 | Emolium Delta/ Gattefosse | 4.00 |
| Dimethicone | DC200 fluid, 100 cst/ Dow Corning | 1.00 |
| C30-38 olefin/isopropyl maleate/MA copolymer | Performa V1608/New Phase Technologies | 1.00 |
| C12-15 alkyl benzoate | Finsolv TN/Finetex | 12.00 |
| Sol-gel capsule containing Butyl methoxydibenzoylmethane, Octylmethoxy cinnamte, and Photostabilizer* | Present Invention | 20.00 |
| Phase C | | |
| Triethanolamine (99%) | | 0.30 |
| Phase D | | |
| Phenoxyethanol, Isopropyl-paraben, Isobutylparaben, Butylparaben | Liquapar PE/Sutton | 1.00 |
| Total | | 100.00 |

*40% Dispersion in water containing about 20% Avobenzone, 20% Photostabilizer (Diethylhexyl 3,5-Dimethoxy-4-hydroxybenylidene malonate) and 60% Octinoxate Procedure Disperse A-2 in A-1 under agitation. Heat A to 70-75° C. Combine B and heat to 70-75° C. Add B to A while stirring.

Add C. Homogenize until mixture cools to 60° C. Add phase D. Stir allowing mixture to cool to RT.

Example 3b

Sunscreen Lotion with sol-gel capsule of Avobenzone, Homosalate & photostabilizer

Procedure is similar as described in Example 4, except Octinoxate is replaced with Homosalate.

Example 9b

Sprayable Sunscreen Lotion with Sol-Gel Capsule of Avobenzone, Solubilizer & Photostabilizer

| INCI NAME | TRADE NAME/ MANUFACTURER | % w/w |
|---|---|---|
| Phase A | | |
| PEG-30 Dipolyhydroxystearate | Arlacel P135/Uniqema | 3.00 |
| Hexyl Laurate | Cetiol A/Cognis | 5.50 |
| Isohexadecane | Arlamol HD | 8.00 |
| Caprylic/Capric Triglyceride | Miglyol 812 N | 4.00 |
| Diocyl Adipate | Crodamol DOA | 4.00 |
| Phase B | | |
| Magnesium Sulfate | Magnesium Sulfate/Merck KGaA | 0.70 |
| Glycerine | Glycerol (about 87%)// Merck KGaA | 3.00 |
| Disodium EDTA | Titriplex III/Merck KGaA | 0.05 |
| Water | | 46.05 |
| Phase C | | |
| Present Invention | Sol-gel capsule containing Butyl methoxydibenzoylmethane, cocoglyceride, and Photostabilizer* | 20.00 |
| Phase D | | |
| Titanium Dioxide, Alumina, Stearic acid | Eusolex TS/Merck KGaA | 5.00 |
| Phase E | | |
| Phenoxyethanol, Isopropylparaben, Isobutylparaben, Butylparaben | Liquapar PE/Sutton | 0.70 |
| Total | | 100.00 |

*40% Dispersion in water containing about 20% Avobenzone, 20% Photostabilizer (Diethylhexyl 3,5-Dimethoxy-4-hydroxybenylidene malonate) and 60% cocoglyceride Procedure Combine phases A and B and heat to 80 C. Add phase B slowly to phase A while stirring vigorously. Homogenize. Allow to cool down while stirring and add phase C at 40 C, disperse Eusolex TS and finally add phase E. Stir to cool.

D. Photostability Studies

This Example shows the effect of Di-2-ethylhexyl-3,5-dimethoxy-4-hydroxy-benzalmalonate (Oxynex ST) on the photostability of Avobenzone. Di-2-ethylhexyl-3,5-dimethoxy-4-hydroxy-benzalmalonate is a yellow viscous liquid having a $\lambda_{max}$ at 332 nm (MeOH, $\epsilon_{max}$ 18,600 cm$^{-1}$ mol$^{-1}$) or 337 nm (EtOH:H$_2$O/70:30, $\epsilon_{max}$ 19,840 cm$^{-1}$ mol$^{-1}$). It has an antioxidant activity (IC$_{50}$=85±8 µg/ml) as determined by the Diphenylpicryl Hydrazide (DPPH) test method.

Method

About 14.8 mg of a formulation are spread evenly on the rough side of a microscopic slide (micro slides, frosted on one surface, size, 76×26 mm, Chance Propper Ltd. Spon Lane, England). After evaporation (20 minutes) slides are weighted and each slide is normalized by a factor to the mean of five plates. Then three slides are irradiated (5 and 10 MED; 5MED: 3 h 19 min; 10MED: 6 h 38 min) and two slides are non-irradiated. After the completion of irradiation, the complete slide containing the mixture is rinsed in methanol and the remaining Avobenzone is analyzed by UV spectral analysis and HPLC.

Selection of Parameters:

| Irradiation dose | Emulsion 1 | Emulsion 2 |
|---|---|---|
| 1,2,5 MED (5 MED = 250 kJ/m$^2$) | OW 3.2 (28% Co-encapsulated Avobenzone with Oxynex ST + HMS) Effective amount in the formulation 2% Avobenzone + 2% Oxynex ST + 6% HMS Control(Un-encapsulated) OW 3.0 (6% HMS, 2% BMDBM) OW 3.1 (6% HMS, 2% BMDBM 2% Oxynex ST) | OW 4.1 (28% Co-encapsulated Avobenzone with Oxynex ST + HMS) + 15% Encapsulated. OMC) Effective amount in the formulation 2% Avobenzone + 2% Oxynex ST + 6% HMS and 5% OMC Control(Un-encapsulated) OW 4.0 (6% HMS, 2% BMDBM, 2% Oxynex ST 5% OMC) |

Determination of degradation of Avobenzone by HPLC

Goal:

The role of co-encapsulation on the photostability of Avobenzone

Results:

% Avobenzone Remaining in the Formulations by HPLC

| | O/W 3.0 6% HMS + 2% Avoben | O/W 3.1 6% HMS + 2% Avoben + 2% Oxynex ST | O/W 3.2 Co-encapsulated material | O/W 4.0 6% HMS + 2% Avobe + 2% Oxyn ST + 5% OMC | O/W 4.1 Co-encapsulated material + Encapsulated OMC |
|---|---|---|---|---|---|
| 50 KJ/m$^2$ | 59.8 | 69.6 | 86.5 | 64.7 | 88.1 |
| 100 KJ/m$^2$ | 41.3 | 57.8 | 66.4 | 42.2 | 53.6 |
| 250 KJ/m$^2$ | 6.0 | 27.8 | 32.4 | 7.4 | 36.4 |

Conclusion:

Co-encapsulation of HMS+Oxynex ST+Avobenzone has a positive effect on the photostability of Avobenzone observed at all MEDs, which is better than the non-encapsulated one. This effect of Avobenzone photostabilization is much more pronounced when the co-encapsulated material is combined with encapsulated OMC.

DPPH Test Method

A DPPH concentrate (2.5×) of 25 mg of 1,1-Diphenyl-2-Picyrl-Hydrazyl ACS#1898-66-4 (Sigma #D-9132, lot 99H3601) dissolved in 250 mL ethanol (USP), is prepared fresh on the measurement date. A DPPH working solution is then prepared by diluting 100 mL of this concentrate to a final volume of 250 mL (100 µM/mL). A blank 13×100 mm borosilicate glass screw top tube of ethanol (USP) is used to zero the spectrometer (Milton Roy, Spectronic 20+) at 517 nm and a control tube of DPPH working solution is measured under identical conditions, and taken as 0% activity. Aliquots of the 0.25% & 0.5% (RT & 45° C.) test solution are added to tubes followed by the rapid addition of 4 mL DPPH working solution then rapidly capped and mixed. After 20 minutes, the absorbance of each sample is read at 517 nm.

The percent reducing activity (% RA) is calculated using the following equation:

$$\% \text{Reduction Activity} = 100 \frac{A(0) - A(20)}{A(0)}$$

Where $A(0)$ is the absorbance value of the DPPH working solution at 517 nm zeroed against an ethanol blank and $A(20)$ is the absorbance at 517 nm, 20 minutes after combining the antioxidant with the DPPH working solution.

The concentration of antioxidant (mg/ml) in the final assay mixture is calculated based on the dilution of respective aliquots of each compound in the final assay volume and % RA tabulated and plotted as percent activity at each concentration in the dilution series:

Photostabilization of Avobenzone (in formulation) was performed using thin films (about 50-100µ thick, transmission signals in the non-absorbing regions must be above 85%) of formulated materials placed between two glass slides and then irradiated under UV-B light (Q-U-V Accelerated Weather Tester, The Q Panel Company). Photodegradation of Avobenzone was calculated from the relative loss in absorption of Avobenzone in formulated products before and after irradiation. 1 hour irradiation under UV-B light is equal to about 1.4 MED (minimal erythemal dose). A Beckman Coulter DU-640 spectrophotometer at a scan speed of 120 nm/min was used for this study. All spectra were recorded from 200 to 600 nm. Effectiveness of Oxynex® ST was compared with Corapan TQ (Di-2-ethylhexyl-napthylate, H&R). Photostabilization of Avobenzone in HMS with Oxynex® ST or TQ in formulation was determined by using a ratio (w/w) of 2:6:2.

A three fold (from 24% to 81%) increase in Avobenzone stability in the presence of Oxynex® ST photostabilizer (1:1, w/w) was observed. Further improvement in Avobenzone stabilization was seen when Oxynex® ST was used at a 1:2 or 1:3 ratio. TQ, on the other hand, had practically no effect on the photostabilization of Avobenzone when used alone. TQ also failed to stabilize Avobenzone when combined with Homosalate. However, the stabilization efficiency of Oxynex® ST on Avobenzone in the presence of HMS was about three-fold higher (from 14% to 56%). Oxynex ST also improves the photostability of Avobenzone in the presence of OMC by two-fold (from 36% to 73%).

In vitro studies showed, Avobenzone (2%) in the presence of HMS (6%) and Oxynex®. ST (2%) had the appropriate critical wavelength and SPF (>30).

The solubility of Avobenzone was tested in various ratios of Oxynex® ST and HMS. The results are summarized below.

TABLE I

Solubility of Avobenzone in the Oxynex ® ST Photostabilizer + HMS

| Avobenzone | Oxynex ® ST | HMS | Storage Temp | 24 hr | 1 week | 2 weeks | 3 weeks | 6 weeks |
|---|---|---|---|---|---|---|---|---|
| 15 | 15 | 70 | RT | Clear | Clear | Clear | Clear | Clear |
|  |  |  | 4° C. | Clear | Clear | Crystal? | Crystal? | Ppt |
| 20 | 20 | 60 | RT | Clear | Clear | Clear | Clear | Clear |
|  |  |  | 4° C. | Clear | Clear | Crystal? | Crystal? | Ppt |
| 25 | 25 | 50 | RT | Clear | Clear | Crystal? | Ppt | Ppt |
|  |  |  | 4° C. | Clear | Ppt | Ppt | Ppt | Ppt |
| 30 | 30 | 40 | RT | Clear | Ppt | Ppt | Ppt | Ppt |
|  |  |  | 4° C. | Clear | Ppt | Ppt | Ppt | Ppt |

Ppt = precipitate

Considering the solubility of Avobenzone in different rations of HMS and Oxynex® ST, the following ratios for encapsulation of Avobenzone (UV-Pearl Avo) using the Sol-Gel process are preferred: Avobenzone/Oxynex® ST/HMS: 20/20/60 and 25/25/50.

TABLE II

Solubility of Avobenzone in the Oxynex ® ST Photostabilizer + OMC

| Avobenzone | Oxynex ® ST | OMC | Storage Temp | 48 hr | 1 week | 2 weeks |
|---|---|---|---|---|---|---|
| 20 | 20 | 60 | RT | Clear | Clear | Clear |
|  |  |  | 4° C. | Clear | Clear | Crystal? |
| 25 | 25 | 50 | RT | Clear | Clear | Crystal? |
|  |  |  | 4° C. | Clear | Ppt | Ppt |
| 30 | 20 | 50 | RT | Few Crystals | | |
|  |  |  | 4° C. | Few Crystals | | |

Ppt = precipitate

Considering the solubility of Avobenzone in different rations of OMC and Oxynex® ST, the following ratios for encapsulation of Avobenzone (UV-Pearl Avo) using the Sol-Gel process are preferred: Avobenzone/Oxynex® ST/OMC: 20/20/60 and 25/25/50.

The preceding examples can be repeated with similar success by substituting the generically or specifically described reactants and/or operating conditions of this invention for those used in the examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A sunscreen capsule comprising
   i) at least one UV-A organic sunscreen
   and
   ii) at least one photostabilizer that is a compound of formula I or II,

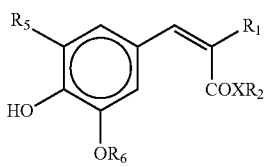

wherein
$R_1$ is —C(O)CH$_3$, —CO$_2$R$_3$, —C(O)NH$_2$, or —C(O)N(R$_4$)$_2$;
X is O or NH or N—C$_{1-8}$-Alkyl;
$R_2$ is linear or branched C$_1$ to C$_{20}$ alkyl;
$R_3$ is linear or branched C$_1$ to C$_{20}$ alkyl; and
each $R_4$ is independently hydrogen or linear or branched C$_1$ to C$_8$ alkyl,
$R_5$ is hydrogen or linear or branched C$_1$-C$_8$ alkyl or linear or branched C$_1$-C$_8$ alkoxy,
and
$R_6$ is independently linear or branched C$_1$-C$_8$ alkyl.

2. A sunscreen capsule according to claim 1, wherein —R$_5$ and —O—R$_6$ are independently of each other selected from linear or branched C$_1$-C$_8$ alkoxy radicals.

3. A sunscreen capsule according to claim 1, wherein the at least one compound of formula II is at least one compound selected from the compounds of formula V or VI

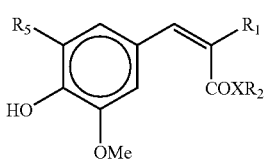

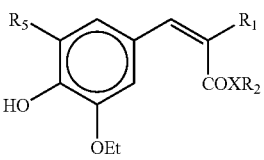

wherein
$R_1$ is —C(O)CH$_3$, —CO$_2$ (C$_1$-C$_8$ alkyl), —C(O)NH$_2$, or —C(O)N(C$_1$-C$_4$ alkyl)$_2$;
X is O or NH or N—C 1-8-alkyl; and
$R_2$ is C$_1$-C$_{12}$ alkyl, and
$R_5$ is C$_1$-C$_8$ linear or branched alkyl.

4. A sunscreen capsule according to claim 1, wherein —R$_5$ and —O—R$_6$ are independently of each other linear or branched C$_1$-C$_4$ alkoxy.

5. A sunscreen capsule according to claim 1, wherein X is oxygen and R$_2$ is preferably linear or branched C$_1$-C$_4$ alkyl.

6. A sunscreen capsule according to claim 1, wherein R$_1$ is CO$_2$R$_3$, preferably C(O)CH$_3$, and, R$_3$ is linear or branched C$_1$ to C$_4$ alkyl.

7. A sunscreen capsule according to claim 1, wherein R$_1$ is —C(O)N(R$_4$)$_2$, and at least one R$_4$ is hydrogen and the other is hydrogen or linear or branched C$_1$ to C$_4$ alkyl.

8. A sunscreen capsule according to claim 1, wherein R$_1$ is —C(O)N(R$_4$)$_2$, and each R$_4$ is independently linear or branched C$_1$ to C$_4$ alkyl.

9. A sunscreen capsule according to claim 1, wherein at least one of R$_2$ and R$_3$ is linear or branched C$_8$ to C$_{20}$ alkyl.

10. A sunscreen capsule according to claim 1, wherein said compound of formula II is
    ethyl-alpha-acetyl-3,5-dimethoxy-4-hydroxy cinnamate,
    iso-propyl-alpha-acetyl-3,5-dimethoxy-4-hydroxy cinnamate,
    iso-amyl-alpha-acetyl-3,5-dimethoxy-4-hydroxy cinnamate,
    2-ethylhexyl-alpha-acetyl-3,5-dimethoxy-4-hydroxy cinnamate,
    diethyl-3,5-dimethoxy-4-hydroxy benzylidene malonate,
    di-(2-ethylhexyl)-3,5-dimethoxy-4-hydroxy benzylidene malonate,
    diisoamyl-3,5-dimethoxy-4-hydroxy benzylidene malonate,
    dipalmitoyl-3,5-dimethoxy-4-hydroxy benzylidene malonate,
    di-do decyl-3,5-dimethoxy-4-hydroxy benzylidene malonate,
    di-isopropyl-3,5-dimethoxy-4-hydroxy benzylidene malonate,
    ethyl-alpha-acetyl-3-methoxy-4-hydroxy cinnamate,
    iso-propyl-alpha-acetyl-3-methoxy-4-hydroxy cinnamate,
    iso-amyl-alpha-acetyl-3-methoxy-4-hydroxy cinnamate,
    2-ethylhexyl-alpha-acetyl-3-methoxy-4-hydroxy cinnamate,
    diethyl-3-methoxy-4-hydroxy benzylidene malonate,
    di-(2-ethylhexyl)-3-methoxy-4-hydroxy benzylidene malonate,
    diisoamyl-3-methoxy-4-hydroxy benzylidene malonate,
    dipalmitoyl-3-methoxy-4-hydroxy benzylidene malonate,
    di-dodecyl-3-methoxy-4-hydroxy benzylidene malonate,
    di-isopropyl-3-methoxy-4-hydroxy benzylidene malonate,
    di-(2-ethyhexyl)-3-methoxy-4-hydroxy-5-isopropyl-benzylidene malonate,
    di-isoamyl-3-methoxy-4-hydroxy-5-tert.butyl-benzylidene malonate,
    iso-amyl-alpha-acetyl-3-methoxy-4-hydroxy-5-isopropyl cinnamate,
    or
    iso-amyl-alpha-acetyl-3-methoxy-4-hydroxy-5-tert.butyl cinnamate.

11. A sunscreen capsule according to claim 1, wherein the capsule is prepared by sol gel encapsulation and the wall of said capsule consists essentially of silica gel and/or silica.

12. A sunscreen capsule according to claim 11, wherein the capsule wall is mainly composed of organopolysiloxane.

13. A sunscreen capsule according to claim 1, wherein the at least one UV-A organic sunscreen is: 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, or 2,6-dimethyl-4-tert-butyl-4'-methoxydibenzoylmethane.

14. A sunscreen capsule according to claim 1, which comprises from 0.1 to 40 wt. % of at least one compound of formula II.

15. A sunscreen capsule according to claim 1, wherein the capsule further comprises at least one UV-B liquid organic sunscreen that is a salicylate or a cinnamate or being a combination thereof, and/or at least one solubilizer that is an ester, a long chain fatty acid or an alcohol.

16. A sunscreen capsule according to claim 1, comprising
i) at least one UV-A organic sunscreen 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethyldibenzoylmethane, 4-tert-butyl-4'-methoxydibenzoylmethane, -2-methyl-5-isopropyl-4'-methoxydibenzoylmethane, 2-methyl-5-tert-butyl-4'-methoxydibenzoylmethane, 2,4-dimethyl-4-methoxydibenzoylmethane, or 2,6-dimethyl-4-tert-butyl-4'-methoxydibenzoylmethane; and
ii) at least one compound of formula II that is ethyl-alpha-acetyl-3,5-dimethoxy-4-hydroxy cinnamate, iso-propyl-alpha-acetyl-3,5-dimethoxy-4-hydroxy cinnamate, iso-amyl-alpha-acetyl-3,5-dimethoxy-4-hydroxy cinnamate, 2-ethylhexyl-alpha-acetyl-3,5-dimethoxy-4-hydroxy cinnamate, diethyl-3,5-dimethoxy-4-hydroxy benzylidene malonate, di-(2-ethylhexyl)-3,5-dimethoxy-4-hydroxy benzylidene malonate, diisoamyl-3,5-dimethoxy-4-hydroxy benzylidene malonate, dipalmitoyl-3,5-dimethoxy-4-hydroxy benzylidene malonate, di-dodecyl-3,5-dimethoxy-4-hydroxy benzylidene malonate, or di-isopropyl-3,5-dimethoxy-4-hydroxy benzylidene malonate.

17. A sunscreen capsule according to claim 1, wherein said at least one UV-A organic sunscreen and said at least one photostabilizer are present in a weight-ratio from about 3:1 to about 1:3.

18. A sunscreen capsule according to claim, 1, wherein said photostabilizer preferably is di-2-ethylhexyl-3,5 dimethoxy-4-hydroxy-benzalmalonate.

19. A composition for topical application that comprises
i) at least one capsule according to claim 1 and
ii) a carrier suitable for topical application.

20. A composition for topical application according to claim 19, that further comprises:
iii) at least one adjuvant that is a preservative, an antifoam agent, a perfume, an oil, a wax, a propellant, a dye, a pigment, a waterproofing agent, an emulsifier, a surfactant, a thickener, a humectant, an exfoliant or an emollient.

21. A composition for topical application according to claim 19, which is a cream, an ointment, a suspension, a powder, an oily lotion, an oleo-alcoholic lotion, a fatty gel, an oleo-alcoholic gel, a solid stick, a foam, an emulsion, a liquid dispersion, a spray, an aerosol, a lipstick, a foundation, a make-up, a loose or pressed powder, an eye blush, an eye shadow or a nail lacquer.

22. A composition for topical application according to claim 19, which comprises at least one additional organic sunscreen agent for filtering UV-B rays, UV-A rays or both.

23. A composition for topical application according to claim 19, which comprises at least one additional antioxidant.

24. A method of protecting a substrate from UV radiation which comprises applying a composition according to claim 19 to said substrate.

25. A method of protecting a substrate from UV radiation according to claim 24, wherein the substrate is skin or hair.

26. A method of protecting a substrate from UV radiation according to claim 24, wherein the substrate is paint, a fiber, wood, plastic, a polymer, color, or a colored wax-based article.

27. A method of producing a sunscreen capsule by mixing at least one UV-A organic sunscreen and at least one photostabilizer that is a compound of formula II,

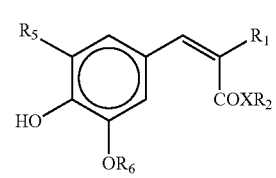

wherein
$R_1$ is —C(O)CH$_3$—C(O)NH$_2$, or —C(O)N(R$_4$)$_2$;
X is O or NH or N—C$_{1-8}$-Alkyl;
$R_2$ is linear or branched C$_1$ to C$_{20}$ alkyl;
$R_3$ is linear or branched C$_1$ to C$_{20}$ alkyl; and
each $R_4$ is independently hydrogen or linear or branched C$_1$ to C$_8$ alkyl,
$R_5$ is hydrogen or linear or branched C$_1$-C$_8$ alkyl or linear or branched C$_1$-C$_8$ alkoxy,
and
$R_6$ is independently linear or branched C$_1$-C$_8$ alkyl;
with a precursor material for the capsule wall and forming the wall by condensing the precursor.

28. A method according to claim 27, wherein the condensation of the precursor occurs during a sol gel process.

29. A method according to claim 27, wherein the precursor is a polysiloxane prepolymer.

30. A method of producing a composition for topical application by mixing at least one capsule according to claim 1 and a carrier suitable for topical application.

31. A composition for topical application according to claim 23, wherein said antioxidant is a tocopherol, tocopherylacetate, ascorbic acid, an emblica antioxidant, a proanthocyanidin, a rosemary antioxidant, a green tea polyphenol, gallic acid, ellagic acid, butylhydroxy toluene (BHT) or butylhydroxy anisole (BHA).

32. A composition for topical application according to claim 22, wherein the additional organic sunscreen agent for filtering UV-B rays, UV-A rays or both is encapsulated.

33. A sunscreen capsule according to claim 13, wherein said organopolysiloxane is synthesized by polycondensing one or more compounds of formula: $R_nSi(OH)_mY_{(4-m-n)}$
wherein, m represents an integer from 1 to 4 and n represents an integer from 0 to 3 with the condition that m+n≦4; R represents an organic group in which a carbon atom is directly connected to a silicone atom, and when n is greater than 1, each of the R groups may be the same or different; and Y represents at least one group that is an alkoxy group, hydrogen or a siloxy group, and when (4-m-n) is greater than 1, each of the groups Y may be the same or different.

34. A sunscreen capsule according to claim 17, wherein said at least one UV-A organic sunscreen and said at least one photostabilizer are present in a weight-ratio from about 1:0.8 to 1:2.

35. A sunscreen capsule according to claim 2, wherein the at least one compound of formula II is a compound of formula III or IV

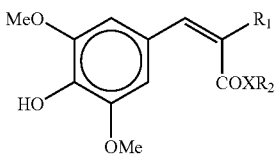

III

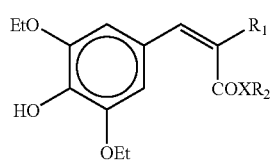

IV wherein
$R_1$ is —C(O)CH$_3$, —CO$_2$ (C$_1$-C$_8$ alkyl), —C(O)NH$_2$, —C(O)NH(C$_1$-C$_4$ alkyl), or —C(O)N(C$_1$-C$_4$ alkyl)$_2$;
X is O or NH or N—C$_{1-8}$-Alkyl;
and
$R_2$ is C$_1$-C$_{12}$ alkyl.

36. A sunscreen capsule according to claim 4, wherein —R$_5$ and —O—R$_6$ are identical and are either methoxy or ethoxy.

37. A sunscreen capsule according to claim 9, wherein R$_2$ and R$_3$ are each linear or branched C$_8$ alkyl or at least one of R$_2$ and R$_3$ is linear or branched C$_{12}$ to C$_{20}$ alkyl.

* * * * *

UNITED STATES PATENT AND TRADEMARK OFFICE
CERTIFICATE OF CORRECTION

| | | |
|---|---|---|
| PATENT NO. | : 8,003,082 B2 | Page 1 of 1 |
| APPLICATION NO. | : 10/559291 | |
| DATED | : August 23, 2011 | |
| INVENTOR(S) | : Chaudhuri | |

It is certified that error appears in the above-identified patent and that said Letters Patent is hereby corrected as shown below:

Column 35, line 16, reads "mula I or II, should read -- mula II, --

Column 37, line 31, reads "methoxydibenzoylmethane, 2,4-dimethyl-4-"
should read -- methoxydibenzoylmethane, 2,4-dimethyl-4'- --

Column 38, line 33 reads "$R_1$ is -C(O)CH$_3$-C(O)NH$_2$, or -C(O)N(R$_4$)$_2$;"
should read -- $R_1$ is -C(O)CH$_3$,-CO$_2$R$_3$,-C(O)NH$_2$, or -C(O)N(R$_4$)$_2$; --

Signed and Sealed this
Twenty-ninth Day of November, 2011

David J. Kappos
*Director of the United States Patent and Trademark Office*